United States Patent
Nakazawa

(10) Patent No.: US 10,383,554 B2
(45) Date of Patent: Aug. 20, 2019

(54) KINETIC ANALYSIS SYSTEM

(71) Applicant: Konica Minolta, Inc., Tokyo (JP)

(72) Inventor: Masayuki Nakazawa, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 297 days.

(21) Appl. No.: 15/620,271

(22) Filed: Jun. 12, 2017

(65) Prior Publication Data
US 2017/0367624 A1 Dec. 28, 2017

(30) Foreign Application Priority Data

Jun. 23, 2016 (JP) .................................. 2016-124841

(51) Int. Cl.
*A61B 5/11* (2006.01)
*A61B 5/113* (2006.01)
*A61B 6/00* (2006.01)

(52) U.S. Cl.
CPC ............ *A61B 5/1128* (2013.01); *A61B 5/113* (2013.01); *A61B 6/463* (2013.01); *A61B 6/486* (2013.01); *A61B 6/50* (2013.01); *A61B 6/5217* (2013.01); *A61B 6/541* (2013.01)

(58) Field of Classification Search
CPC ....... A61B 5/1128; A61B 5/113; A61B 6/463; A61B 6/486; A61B 6/50; A61B 6/5217; A61B 6/541
See application file for complete search history.

(56) References Cited

U.S. PATENT DOCUMENTS

| | | | | |
|---|---|---|---|---|
| 6,915,151 B2 * | 7/2005 | Baumgardner | .... | G01R 33/5601 324/307 |
| 7,127,028 B2 * | 10/2006 | Sendai | ................... | A61B 6/025 378/21 |
| 7,158,661 B2 * | 1/2007 | Inoue | ....................... | A61B 6/02 382/128 |
| 7,901,348 B2 * | 3/2011 | Soper | ................... | A61B 1/0008 600/117 |
| 8,300,912 B2 * | 10/2012 | Sanada | ............... | A61B 5/0205 378/69 |
| 8,447,380 B2 * | 5/2013 | Kuth | ....................... | A61B 5/08 600/410 |

(Continued)

FOREIGN PATENT DOCUMENTS

JP 2009153678 A 7/2009

*Primary Examiner* — Manav Seth
(74) *Attorney, Agent, or Firm* — Lucas & Mercanti, LLP

(57) ABSTRACT

A kinetic analysis system includes: an analytical value calculation unit configured to divide, into a plurality of divisions, a lung field region included in kinetic images in a plurality of time phases acquired as a result of kymography of a chest of an object, and calculate analytical values of the respective divisions in the plurality of time phases based on at least one of pixel signal values and the number of pixels in the respective divisions; a ventilation state calculation unit configured to calculate index values representing ventilation states of the respective divisions from the analytical values of the respective divisions in the plurality of time phases using different functions corresponding to the respective divisions; a display unit; and a control unit configured to cause the display unit to display the index values representing the ventilation states of the respective divisions in the plurality of time phases.

16 Claims, 17 Drawing Sheets

(56) References Cited

U.S. PATENT DOCUMENTS

| | | | | |
|---|---|---|---|---|
| 8,483,456 B2* | 7/2013 | Nagatsuka | ............... | A61B 5/08 |
| | | | | 382/128 |
| 8,488,738 B2* | 7/2013 | Morita | ................... | A61B 6/583 |
| | | | | 378/62 |
| 8,798,343 B2* | 8/2014 | Kabus | ................. | A61B 6/5235 |
| | | | | 378/65 |
| 8,911,709 B2* | 12/2014 | Driehuys | ................ | A61B 5/055 |
| | | | | 424/9.3 |
| 8,953,739 B2* | 2/2015 | Maeda | ................... | A61B 6/032 |
| | | | | 378/8 |
| 9,044,194 B2* | 6/2015 | Noji | ......................... | A61B 5/08 |
| 9,125,621 B2* | 9/2015 | Nagatsuka | ............... | A61B 5/08 |
| 9,237,877 B2* | 1/2016 | Noji | ......................... | A61B 5/08 |
| 2003/0190067 A1* | 10/2003 | Tsujii | ...................... | A61B 6/02 |
| | | | | 382/132 |
| 2006/0239530 A1* | 10/2006 | Oosawa | ................ | G06T 7/0012 |
| | | | | 382/130 |

* cited by examiner

KINETIC ANALYSIS SYSTEM

The entire disclosure of Japanese Patent Application No. 2016-124841 filed on Jun. 23, 2016 including description, claims, drawings, and abstract are incorporated herein by reference in its entirety.

BACKGROUND OF THE INVENTION

Field of the Invention

The present invention relates to a kinetic analysis system.

Description of the Related Art

In related art, a device for analyzing X-ray kinetic images or the like to provide information effective in the diagnosis of lung ventilation capacity has been disclosed. For example, JP 2009-153678 A describes a kinetic analysis system. Specifically, information on the absolute ventilation volume between a maximal expiratory phase and a maximal inspiratory phase is acquired, and the estimated ventilation volume per unit signal variation amount is calculated from the absolute ventilation volume and the amount of signal value variation between frame images in the maximal expiratory phase and the maximal inspiratory phase among kinetic images. Then, the signal value variation amount in each time phase from the maximal expiratory phase or the maximal inspiratory phase is multiplied by a value of the estimated ventilation volume per unit signal variation amount, whereby the estimated ventilation volume in each time phase is calculated and provided.

In the lung field, the ventilation volume of the upper lung field is different from that of the lower lung filed. Specifically, as illustrated in a front view of FIG. 15, the lower part of the lung field close to the diaphragm has a large ventilation volume since the variation in the height direction is large. In contrast, the upper part of the lung field distant from the diaphragm has a small ventilation volume since the variation in the height direction is small. As illustrated in a side view of FIG. 15, the lower part of the lung field having a wide depth in the front-back direction has a large ventilation volume since the lower part of the lung field naturally has a large capacity. In contrast, the upper part of the lung field having a narrow depth in the front-back direction has a small ventilation volume since the upper part of the lung field naturally has a small capacity.

In this regard, in JP 2009-153678 A, a lung field region included in the kinetic image is divided into a plurality of divisions, and the estimated ventilation volumes that vary in different divisions are calculated. However, it is difficult to obtain information on the absolute ventilation volume of each division, which serves as a basis for the calculation of the estimated ventilation volume of each division, and JP 2009-153678 A only discloses a method of obtaining information on the absolute ventilation volume of the entire lung field. Furthermore, in JP 2009-153678 A, the estimated ventilation volume in each time phase is obtained using the estimated ventilation volume per unit signal variation amount calculated on the basis of the absolute ventilation volume of the entire lung field, with no consideration for the position of each division. Therefore, the estimated ventilation volume does not necessarily represent the ventilation state of each division accurately.

FIG. 16A is a diagram illustrating the signal value variation amounts of divisions A to C (refer to FIG. 7A) of a healthy person in each point of time. FIG. 16B is a diagram illustrating the signal value variation amounts of divisions A to C of a patient with a disease in the division C in each point of time. FIG. 17A is a diagram illustrating ranges of the signal value variation amounts and ranges of the estimated ventilation volumes which are applied when the signal value variation amounts of the respective divisions A to C of the healthy person illustrated in FIG. 16A are converted into the estimated ventilation volumes using the principle of JP 2009-153678 A. FIG. 17B is a diagram illustrating ranges of the signal value variation amounts and ranges of the estimated ventilation volumes which are applied when the signal value variation amounts of the respective divisions A to C of the patient illustrated in FIG. 16B are converted into the estimated ventilation volumes using the principle of JP 2009-153678 A. FIG. 18A is image diagrams representing the estimated ventilation volumes in the respective points of time calculated from the signal value variation amounts of the respective divisions A to C of the healthy person using the function illustrated in FIG. 17A. FIG. 18B is image diagrams representing the estimated ventilation volumes in the respective points of time calculated from the signal value variation amounts of the respective divisions A to C of the patient with the disease in the division C using the function illustrated in FIG. 17B. In FIGS. 18A and 18B, the respective divisions are represented by colors corresponding to the estimated ventilation volumes.

In JP 2009-153678 A, as illustrated in FIGS. 17A and 17B, index values representing the estimated ventilation volumes are calculated from the signal value variation amounts using the function common to all the divisions. As a result, as illustrated in FIG. 17A, the following relation is satisfied: the range of the estimated ventilation volumes of the division A<the range of the estimated ventilation volumes of the division B<the range of the estimated ventilation volumes of the division C, assuming that the following relation is satisfied: the range of the signal value variation amounts of the division A<the range of the signal value variation amounts of the division B<the range of the signal value variation amounts of the division C. Therefore, the estimated ventilation volumes are represented in the images as if the ventilation states varied in different divisions as illustrated in FIG. 18A even though all the divisions function normally. For example, the division A of the lung field illustrated in FIG. 16A has a small signal value variation amount since the absolute ventilation volume of the division A is naturally small, which means that the ventilation function of the division A is not necessarily low. However, undervaluation of the division A in JP 2009-153678 A causes such a misunderstanding that the ventilation of the division A does not sufficiently function as illustrated in FIG. 18A. In a case where the technique of JP 2009-153678 A is applied to the division C on the lower part of the lung field where the ventilation does not sufficiently function as illustrated in FIG. 16B, since the original absolute ventilation volume of the division C is large, the estimated ventilation volumes are expressed in a somewhat large range as illustrated in FIG. 17B even though the ventilation capacity of the division C is actually low. Therefore, the small estimated ventilation volume could neither be expressed nor noticed as illustrated in FIG. 18B.

SUMMARY OF THE INVENTION

An object of the present invention is to grasp a ventilation state of each division of a lung field more accurately.

To achieve the abovementioned object, according to an aspect, a kinetic analysis system reflecting one aspect of the present invention comprises:

an analytical value calculation unit configured to divide, into a plurality of divisions, a lung field region included in kinetic images in a plurality of time phases acquired as a result of kymography of a chest of an object, and calculate analytical values of the respective divisions in the plurality of time phases based on at least one of pixel signal values and the number of pixels in the respective divisions;

a ventilation state calculation unit configured to calculate index values representing ventilation states of the respective divisions from the analytical values of the respective divisions in the plurality of time phases using different functions corresponding to the respective divisions;

a display unit; and a control unit configured to cause the display unit to display the index values representing the ventilation states of the respective divisions in the plurality of time phases.

According to an invention of Item. 2, in the kinetic analysis system of Item. 1, the ventilation state calculation unit preferably calculates the index values representing the ventilation states of the respective divisions from the analytical values of the respective divisions in the plurality of time phases using a function having a large absolute value of a slope for an upper division of the lung field region and using a function having a small absolute value of a slope for a lower division of the lung field region.

According to an invention of Item. 3, in the kinetic analysis system of Item. 1 or 2, the ventilation state calculation unit preferably calculates the index values representing the ventilation states of the respective divisions from the analytical values of the respective divisions in the plurality of time phases using such functions that offset values for the respective divisions in a maximal inspiratory phase and/or a maximal expiratory phase are different from each other.

According to an invention of Item. 4, in the kinetic analysis system of any one of Items. 1 to 3, the kinetic analysis system preferably further comprises:

a storage unit configured to store the functions corresponding to the respective divisions; and an information acquisition unit configured to acquire the functions corresponding to the respective divisions from the storage unit, wherein the ventilation state calculation unit preferably calculates the index values representing the ventilation states of the respective divisions using the functions corresponding to the respective divisions acquired by the information acquisition unit.

According to an invention of Item. 5, in the kinetic analysis system of Item. 4, the storage unit preferably stores a plurality of patterns of combinations of functions corresponding to the respective divisions, the kinetic analysis system preferably further includes a selection unit configured to select, from among the plurality of patterns stored in the storage unit, a pattern that is used by the ventilation state calculation unit for calculation of the index values, and the ventilation state calculation unit preferably calculates the index values of the respective divisions using functions included in the pattern selected by the selection unit.

According to an invention of Item. 6, in the kinetic analysis system of Item. 5, the selection unit preferably selects a pattern that is used by the ventilation state calculation unit for calculation of the index values based on information as to whether the object has been photographed in a standing posture or a lying posture.

According to an invention of Item. 7, in the kinetic analysis system of Item. 6, in a case where the object has been photographed in the standing posture, the selection unit preferably selects such a pattern that a difference between an absolute value of a slope of a function for an upper division of the lung field region and an absolute value of a slope of a function for a lower division of the lung field region is large, as compared with a case where the object has been photographed in the lying posture.

According to an invention of Item. 8, in the kinetic analysis system of any one of Items. 1 to 7, the kinetic analysis system preferably further comprises a setting unit configured to set the functions corresponding to the respective divisions in accordance with user operation.

According to an invention of Item. 9, in the kinetic analysis system of any one of Items. 1 to 8, the ventilation state calculation unit preferably calculates the index values from the analytical values using different functions for an expiratory phase and an inspiratory phase.

According to an invention of Item. 10, in the kinetic analysis system of Item. 9, the ventilation state calculation unit preferably uses such functions that the index value for the expiratory phase increases/decreases as the analytical value increases while the index value for the inspiratory phase decreases/increases as the analytical value increases.

According to an invention of Item. 11, in the kinetic analysis system of any one of Items. 1 to 10, the control unit preferably generates image diagrams indicating the index values of the respective divisions calculated for the respective kinetic images in the plurality of time phases, and serially switches and displays the image diagrams on the display unit in accordance with the time phases.

According to an invention of Item. 12, in the kinetic analysis system of any one of Items. 1 to 11, the functions are preferably linear functions.

According to an invention of Item. 13, in the kinetic analysis system of any one of Items. 1 to 11, the functions are preferably non-linear functions.

According to an invention of Item. 14, in the kinetic analysis system of any one of Items. 1 to 13, the analytical value calculation unit preferably calculates the analytical values based on transmission X-ray intensities in the respective divisions.

According to an invention of Item. 15, in the kinetic analysis system of any one of Items. 1 to 14, the ventilation state calculation unit preferably calculates relative ventilation volumes as the index values.

According to an invention of Item. 16, in the kinetic analysis system of anyone of Items. 1 to 15, the kinetic analysis system preferably further comprises a photographing unit configured to perform the kymography on the chest of the object to generate the kinetic images in the plurality of time phases.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described in detail with reference to the drawings. However, the scope of the invention is not limited to the illustrated examples.

First, the configuration will be described.

Figure 1:
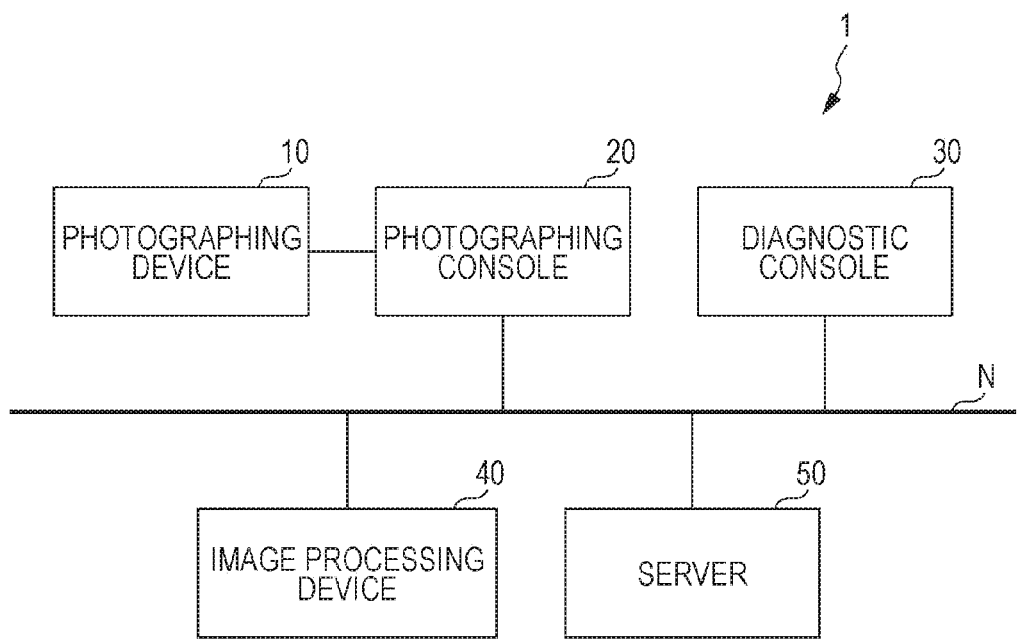
FIG. 1 is a diagram illustrating a kinetic analysis system according to an embodiment.

FIG. 1 is a diagram illustrating a kinetic analysis system 1 according to the present embodiment.

As illustrated in FIG. 1, the kinetic analysis system 1 includes a photographing device 10, a photographing console 20, a diagnostic console 30, an image processing device 40, and a server 50. The photographing device 10 and the photographing console 20 are coupled to each other by a communication cable or the like. The photographing console 20, the diagnostic console 30, the image processing device 40, and the server 50 are coupled to one another via a communication network N such as a local area network (LAN).

Figure 2:
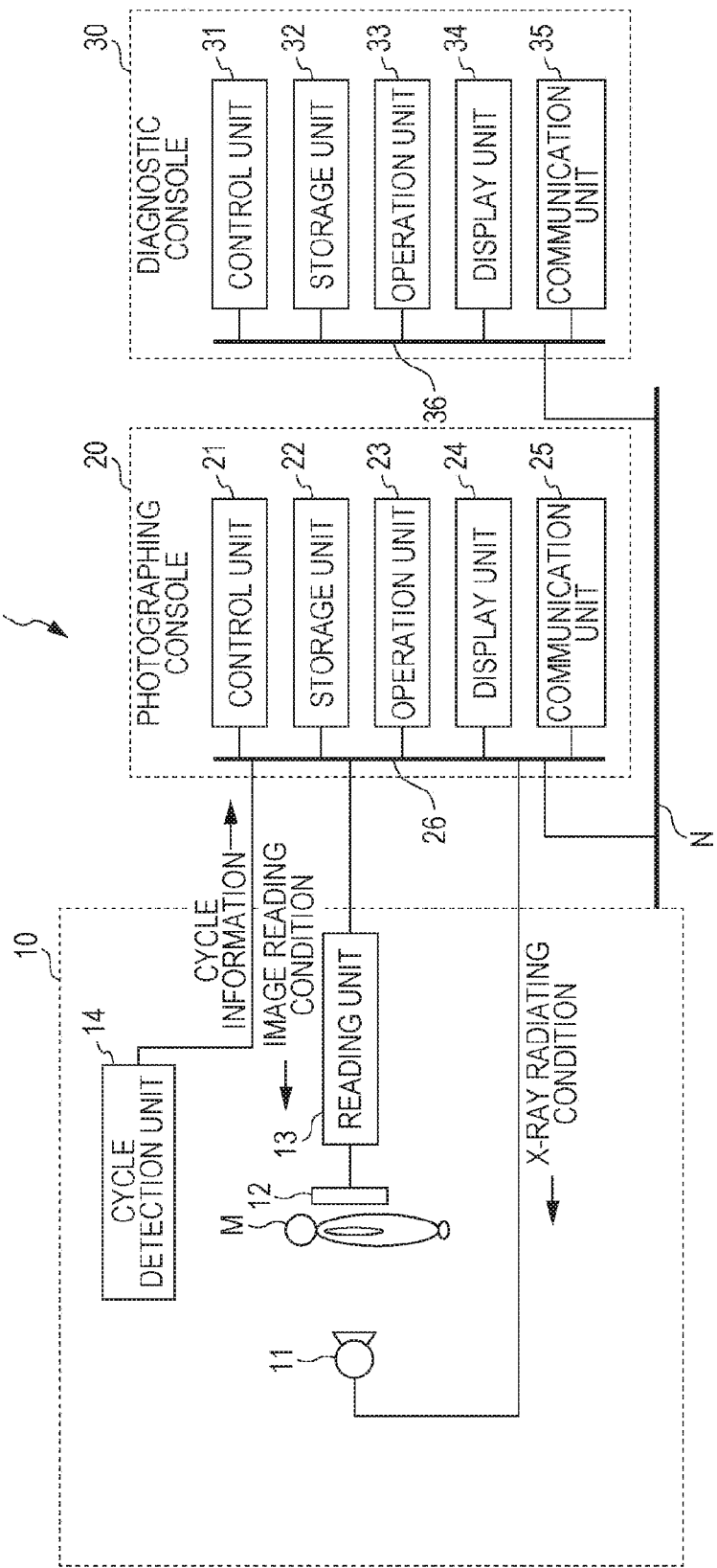
FIG. 2 is a diagram illustrating functional configurations of a photographing device, a photographing console, and a diagnostic console of FIG. 1.

The photographing device 10, the photographing console 20, and the diagnostic console 30 will be further described with reference to FIG. 2. The photographing device 10 includes an X-ray source 11, a detector 12, a reading unit 13, and a cycle detection unit 14. The photographing console 20 includes a control unit 21, a storage unit 22, an operation unit 23, a display unit 24, and a communication unit 25. Similarly, the diagnostic console 30 includes a control unit 31, a storage unit 32, an operation unit 33, a display unit 34, and a communication unit 35.

First, the photographing device 10 will be described.

The photographing device 10 radiates X-rays to an object M, and reads X-ray images from the detector 12. Kymography can be performed using the photographing device 10. The kymography as used herein is a photographing method for serially taking photographs to obtain kinetic images (frame images) in a plurality of time phases. The kinetic images as used herein are photographed images obtained as the result of the kymography. In the present embodiment, the kinetic images are X-ray images.

The X-ray source 11 radiates X-rays in accordance with the control of the control unit 21 of the photographing console 20. Examples of controlled X-ray radiating conditions include a pulse rate, a pulse width, a pulse interval, radiation start/end timings, an X-ray tube current, an X-ray tube voltage, and a filter value or the like, which are applied when kinetic images are serially taken. The pulse rate as used herein is the number of photographing times per unit time. The pulse width as used herein is a period of time during which X-rays are radiated while a single photograph is taken. The pulse interval as used herein is a period of time from the start of X-ray radiation for taking a photograph to the start of X-ray radiation for serially taking a next photograph.

The detector 12 is arranged at a position facing the X-ray source 11 via the object M. The detector 12 is a flat panel detector (FPD) or the like in which detection sensors for X-rays are arranged in a matrix shape. Specifically, since X-rays are converted into electric signals in accordance with the intensities thereof, and accumulated in association with respective pixels (detection sensors), X-ray images are recorded in the detector 12.

The reading unit 13 performs a process for reading the X-ray images from the detector 12, and sends the read X-ray images to the photographing console 20. The reading operation is controlled by the control unit 21. Examples of controlled image reading conditions include a frame rate, a frame interval, and a pixel size or the like. The frame rate and the frame interval have the same meanings as the pulse rate and the pulse interval mentioned above, respectively.

The cycle detection unit 14 detects a vital reaction cycle at a photographing site of the object M. For example, in a case where the photographing site is a chest including lungs as in the present embodiment, a respiratory cycle is detected with a respiration monitoring belt, a CCD camera, an optical camera, and a spirometer or the like.

The cycle detection unit 14 outputs information on the detected cycle to the control unit 21 of the photographing console 20.

Next, the photographing console 20 and the diagnostic console 30 will be described.

The photographing console 20 is used to enable an operator to perform the photographing operation. The photographing console 20 accepts input of photographing conditions or the like, and displays the X-ray images provided by the photographing device 10 so that the operator can confirm them. The diagnostic console 30 is used to enable a doctor to perform the operation. The diagnostic console 30 displays the X-ray images sent from the photographing console 20 so that the doctor can confirm them.

Functions of the respective components of the diagnostic console 30 (the control unit 31, the storage unit 32, the operation unit 33, the display unit 34, and the communication unit 35) are basically the same as those of the respective components of the photographing console 20 (the control unit 21, the storage unit 22, the operation unit 23, the display unit 24, and the communication unit 25). Hereinafter, therefore, the respective components of the photographing console 20 will be described as representatives, and descriptions of the respective components of the diagnostic console 30 will be omitted.

The control unit 21 includes a central processing unit (CPU) and a random access memory (RAM) or the like. The control unit 21 reads various programs stored in the storage unit 22 using the CPU, and extracts the programs to the RAM. The control unit 21 executes a process by performing various computations in cooperation with the extracted programs and performing centralized control on the operation of each component.

The control unit 21 also has a timer function for measuring time by utilizing a CPU clock.

The storage unit 22 is a memory such as a hard disk, and stores the various programs that are used by the control unit 21 and parameters that are required for execution of the programs. For example, photographing conditions (e.g., X-ray radiating conditions and X-ray image reading conditions) optimized for different photographing sites are stored.

The operation unit 23 includes a keyboard and a mouse or the like, generates an operation signal in accordance with the operation therefor, and outputs the operation signal to the control unit 21.

The display unit 24 includes a display to display various operation screens and the X-ray images obtained as the result of the photography in accordance with the display control of the control unit 21.

The communication unit 25 includes a communication interface, and communicates with an external device connected to the network N.

Next, the image processing device 40 and the server 50 will be described.

The image processing device 40 and the server 50 are used for providing the X-ray images obtained as the result of the photography.

Figure 3:
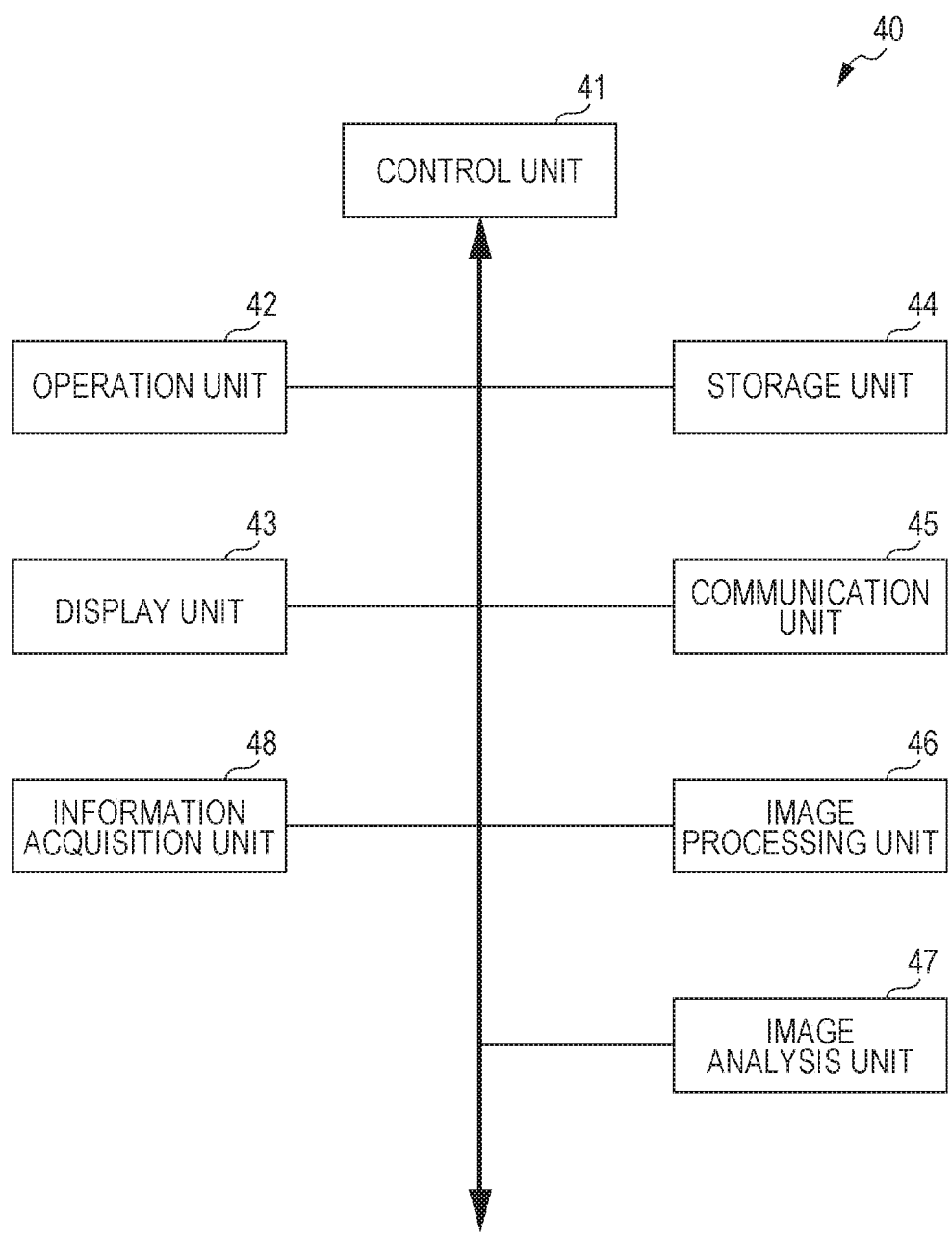
FIG. 3 is a diagram illustrating a functional configuration of an image processing device of FIG. 1.

The image processing device 40 will be described with reference to FIG. 3.

The image processing device 40 performs an image process and an image analysis on the X-ray image. As illustrated in FIG. 3, the image processing device 40 includes a control unit 41, an operation unit 42, a display unit 43, a storage unit 44, a communication unit 45, an image processing unit 46, an image analysis unit 47, and an information acquisition unit 48.

Basic functions of the control unit 41 to the communication unit 45 are the same as those of the control unit 21 to the communication unit 25 of the above-described photographing console 20. Therefore, detailed descriptions are omitted herein. In the storage unit 44, functions for calculating index values Y representing ventilation states from analytical values X are stored in association with respective divisions of a region divided in step S12 of FIG. 5.

The image processing unit 46 performs, on the X-ray image, various image processes such as a gradation conversion process and a frequency adjusting process. The image process of a type corresponding to the photographing site is performed in accordance with an image processing condition corresponding to the photographing site.

The image analysis unit 47 analyzes the kinetic images in the plurality of time phases obtained as the result of the kymography of the chest, and calculates the analytical values X in the respective time phases and the index values Y representing the ventilation states. In other words, the image analysis unit 47 functions as an analytical value calculation unit and a ventilation state calculation unit. A specific calculation method will be described later.

Figure 5:
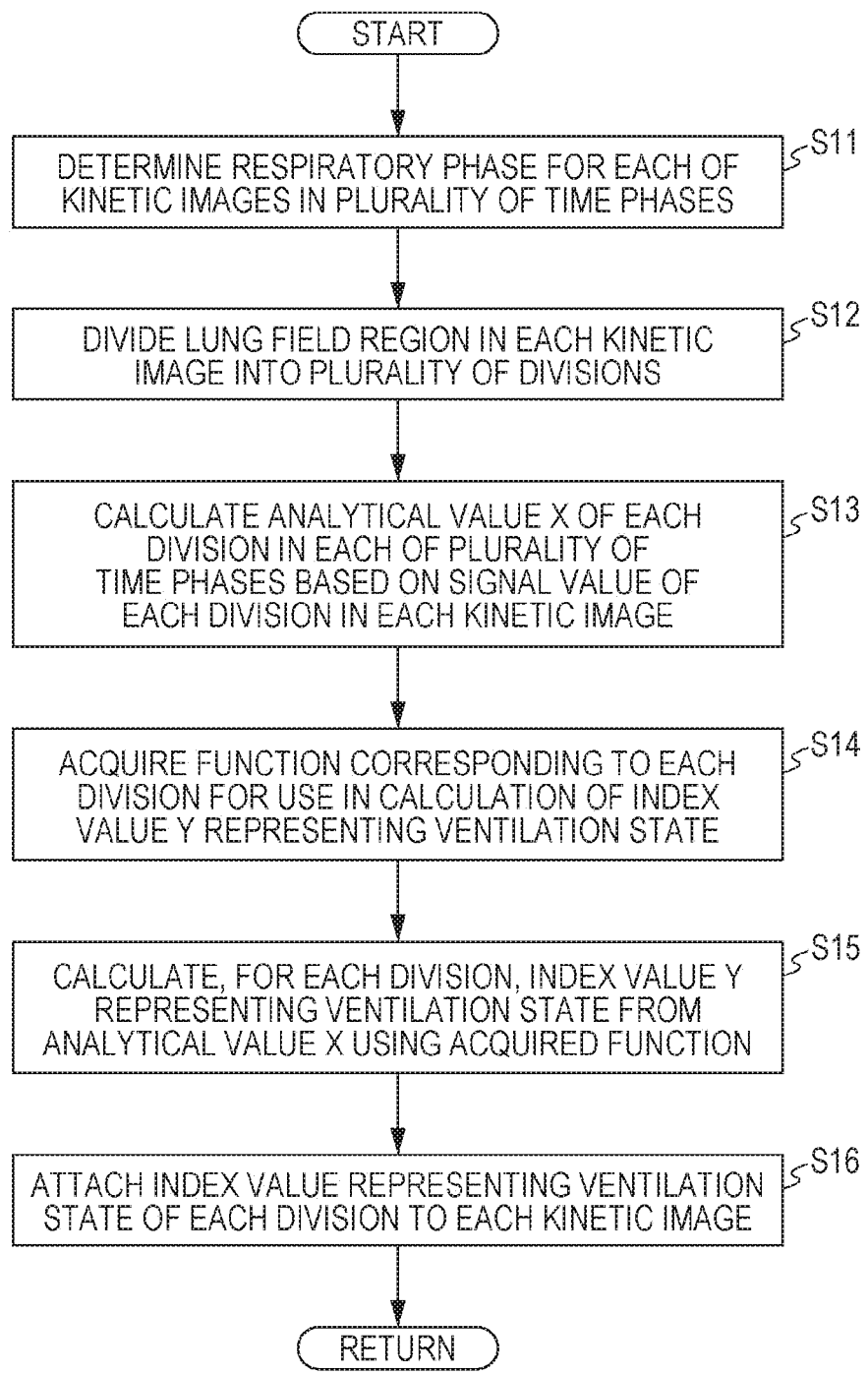
FIG. 5 is a diagram describing a flow of a process for calculating an index value representing a ventilation state.

The information acquisition unit 48 reads and acquires the functions corresponding to the respective divisions of the region divided in step S12 of FIG. 5 from the storage unit 44, and outputs the functions to the image analysis unit 47.

The image processing unit 46, the image analysis unit 47, and the information acquisition unit 48 may be realized by the control unit 41 that operates in cooperation with programs, or may be realized by dedicated hardware.

The server 50 includes a large-capacity memory to save and manage, in the memory, the X-ray images processed by the image processing device 40. The X-ray images saved in the server 50 are delivered in response to a request from the diagnostic console 30 and used for diagnosis.

Next, the operation will be described.

The kinetic analysis system 1 according to the present embodiment performs the kymography on the chest, analyzes the kinetic images obtained in the plurality of time phases, and calculates and displays the index values Y representing the ventilation states in the respective time phases.

Figure 4:
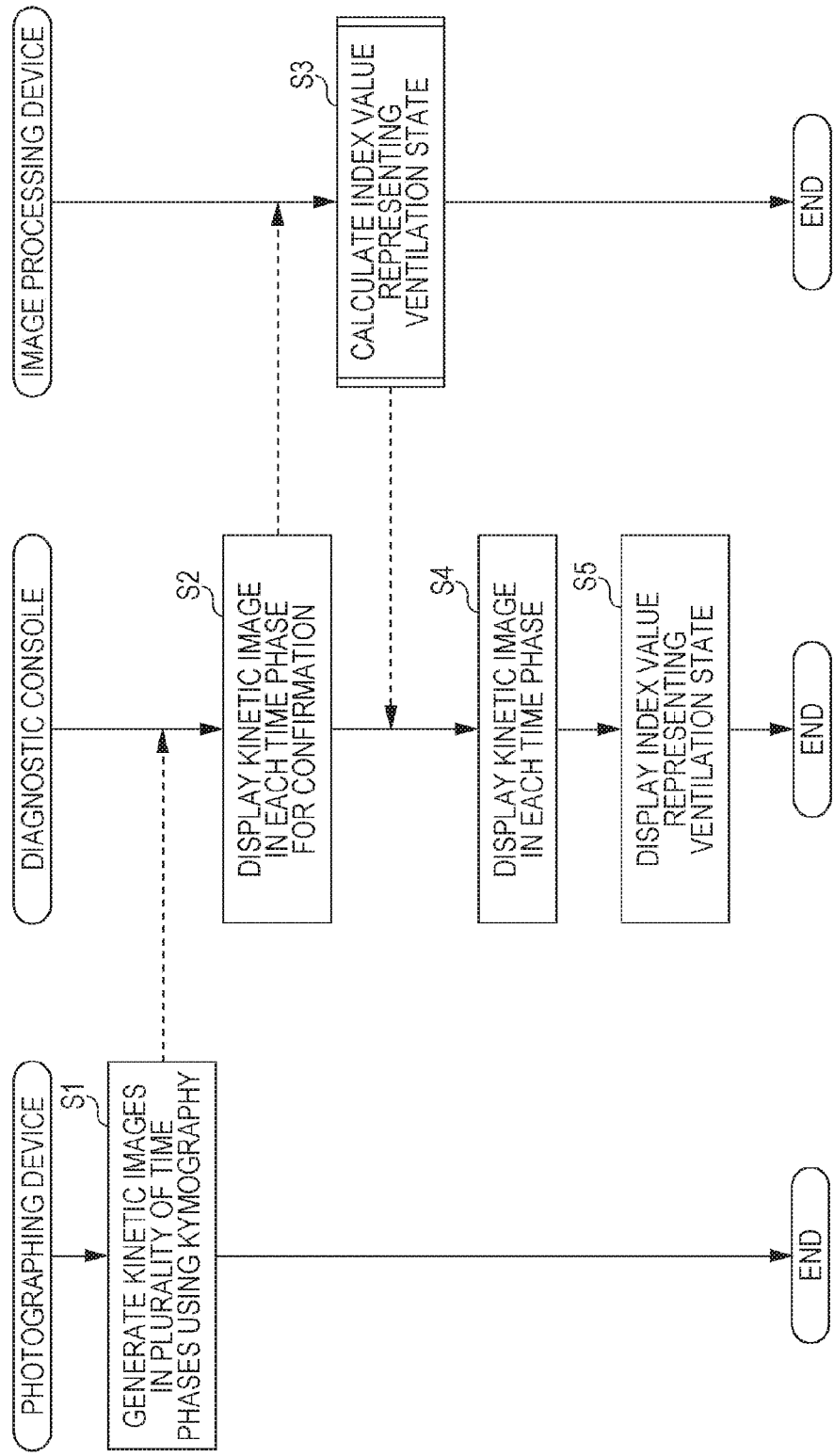
FIG. 4 is a diagram illustrating a flow of a process of the kinetic analysis system.

FIG. 4 is a flowchart illustrating a flow of a process of the photographing device 10, the diagnostic console 30, and the image processing device 40 which perform the main functions in this situation.

First, as illustrated in FIG. 4, the kymography is performed in the photographing device 10, and the kinetic images in the plurality of time phases are generated (step S1). The kymography is performed so that the kinetic images in the plurality of time phases are generated during at least one respiratory phase.

Before taking photographs, a photographing operator inputs patient information about the object M and designates examination information (e.g., photographing site (chest in this example) and body position (standing position, lying position or the like)) via the operation unit 23 of the photographing console 20. Examples of the patient information include information indicating an attribute of the object M, that is, the patient, such as age, gender, weight, and height as well as the patient's name.

In the photographing console 20, the control unit 21 reads the photographing conditions corresponding to the designated photographing site from the storage unit 22, and sets the photographing conditions as the X-ray radiating conditions for the X-ray source 11 of the photographing device 10 and the image reading conditions for the reading unit 13. The following description is based on the assumption that the "chest (lungs)" is designated as the photographing site by the photographing operator. In a case where the lungs are photographed for the examination of lung ventilation capacity, since the respiratory phase is about 0.3 times/second on average, the following exemplary photographing conditions are set so that the kinetic images in the plurality of time phases can be photographed during at least one respiratory phase in consideration of the respiratory cycle.

Frame rate (pulse rate): 3 frames/second (i.e., 3 photographing times per second)

Pixel size: 400 μm

Image size: 40 cm×30 cm

Tube voltage: 120 kV

Tube current: 50 mA

Photographing timing: every frame interval time after the timing of a shift from inspiration to expiration (time to start taking photographs)

The control unit 21 modifies the condition such as the frame rate based on information on the respiratory cycle detected by the cycle detection unit 14. For example, the control unit 21 calculates and resets the frame rate based on the detected respiratory cycle so that a predetermined number of frames (e.g., 10 frames) are photographed during a single respiratory phase. Referring to the above-mentioned exemplary condition for the frame rate, if the respiratory cycle detected by the cycle detection unit 14 is 0.25 times/seconds, the frame rate is modified to 2.5 frames/second.

After setting the photographing conditions, the control unit 21 determines, based on the information on the respiratory cycle detected by the cycle detection unit 14, whether it is time to start taking photographs, that is, whether it is time for a single respiratory phase to begin (for example, shift from inspiration to expiration). The control unit 21 controls the X-ray source 11 and the reading unit 13 to start the kymography when it is time to start taking photographs. Once the kymography is started, the control unit 21 measures a photographing period from the start to the end of the photography.

In the photographing device 10, X-rays are radiated at a predetermined pulse rate in accordance with the set X-ray radiating conditions. Similarly, the reading unit 13 performs the process for reading the X-ray images from the detector 12 at a predetermined frame rate in accordance with the set image reading conditions. The X-ray radiating operation and the image reading operation are synchronized with each other by the control unit 21. Consequently, the kinetic images in the plurality of time phases are generated and output to the photographing console 20.

In the photographing console 20, the kinetic images in the respective time phases obtained as the result of the kymography are displayed on the display unit 24 under the display control of the control unit 21. This enables the photographing operator to confirm image quality or the like. In response to approval operation being performed by the photographing operator via the operation unit 23, the control unit 21 attaches, to each of the kinetic images in the respective time phases, an ID for identifying a series of photographs, a number indicating photographing order, the patient information, the examination information, and information on the photographing period or the like, and sends the kinetic images to the diagnostic console 30. In the diagnostic console 30, the kinetic images are displayed for confirmation in a similar manner (step S2). In response to approval operation, the kinetic images in the respective time phases are sent to the image processing device 40.

In the image processing device 40, the image process corresponding to the photographing site (chest in this example) is performed by the image processing unit 46 on the kinetic images in the respective time phases, and the process for calculating the index values Y representing the ventilation states is performed by the image analysis unit 47 on the kinetic images in the respective time phases (step S3).

The process for calculating the index values Y representing the ventilation states will be described with reference to FIG. 5.

Figure 6:
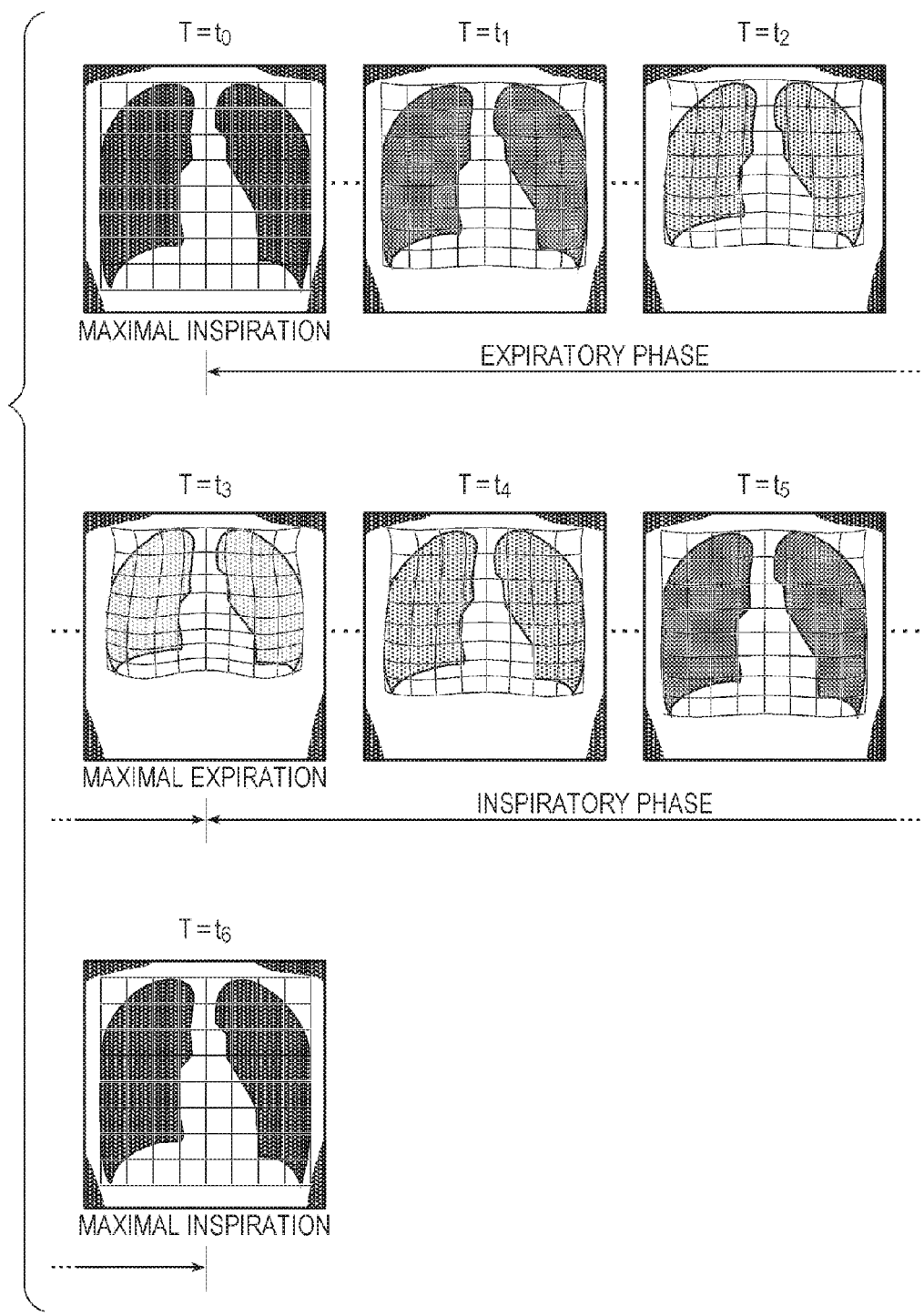
FIG. 6 is a diagram illustrating kinetic images in a plurality of time phases.

First, as illustrated in FIG. 5, the image analysis unit 47 determines the respiratory phase for each of the kinetic images in the plurality of time phases (step S11). Since the lower part of the lung contracts at the time of expiration and expands at the time of inspiration, the image analysis unit 47 calculates the area (the number of pixels) of the lung field region in the kinetic image in each time phase, and determines that the kinetic images in the time phases from a point of the maximal area to a point of the minimal area are in the expiratory phase, and the kinetic images in the time phases from a point of the minimal area to a point of the maximal area are in the inspiratory phase. The result of determining the respiratory phase for the kinetic image in each time phase T ($T=t_0$ to $t_6$) is illustrated in FIG. 6.

Any method may be applied to the recognition of the lung field region. For example, a threshold value is obtained from a histogram of signal values of a reference image using a discriminant analysis, and a region with signal values higher than the threshold value is primarily detected as the lung field region. Next, edges are detected in the vicinity of a boundary of the primarily detected region, and a point of the maximum edge is extracted from each small division along the boundary, whereby a boundary of the lung field region can be detected.

Next, the image analysis unit 47 divides the lung field region in each kinetic image into a plurality of divisions (step S12).

Figure 7A:
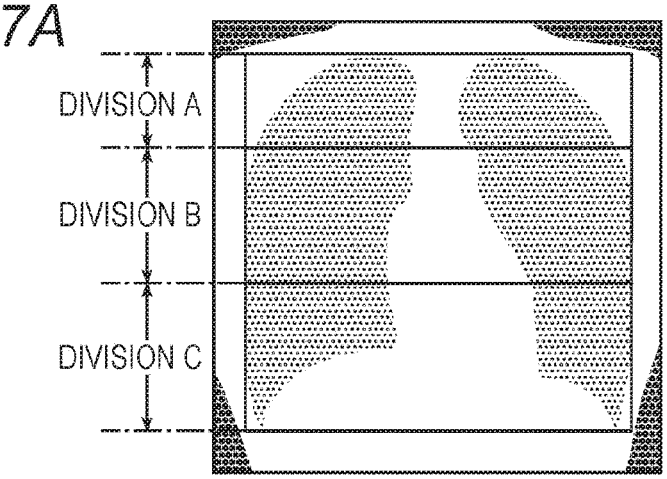
FIGS. 7A to 7C are diagrams illustrating exemplary ways to divide a region.
Figure 7B:
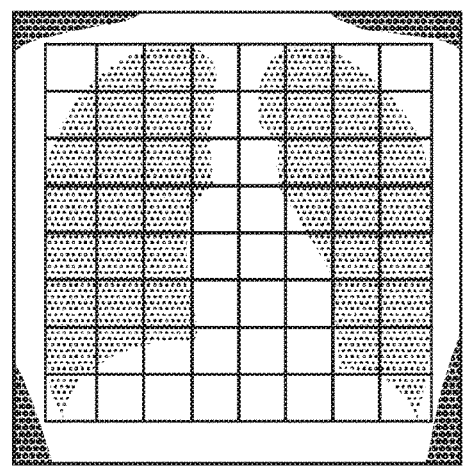

In the present embodiment, the lung field region is divided into three divisions (divisions A, B, and C from above) in the vertical direction as illustrated in FIG. 7A. This is because the absolute ventilation volume of the upper lung field is different from that of the lower lung field as mentioned above. Alternatively, the lung field region may be divided into a plurality of small divisions (for example, 0.4 to 4 cm square) as illustrated in FIG. 7B.

The respective divisions among the kinetic images in the plurality of time phases can be correlated with one another using a local matching method. The local matching method includes selecting one of the kinetic images (e.g., image in the maximal expiratory phase) as a reference image and correlating each of divisions of the reference image with a division of another kinetic image having a high degree of matching. The degree of matching as used herein is the degree indicating consistency between images, and can be obtained using a least-square technique or a cross-correlation technique.

Figure 7C:
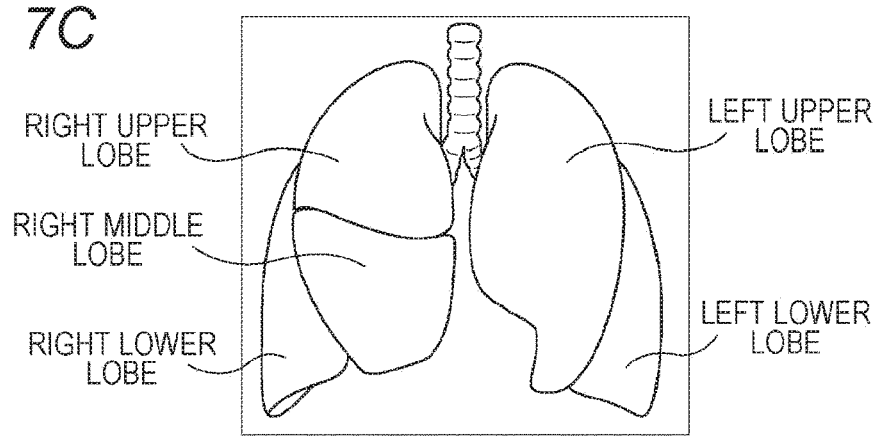

Alternatively, the lung field region may be divided into anatomical structures of the lungs such as a right upper lobe and a left upper lobe as illustrated in FIG. 7C. In this case, the ventilation state of each anatomical structure can be grasped. The lung field region may be divided into the anatomical structures using a reference image including positions and names of the anatomical structures defined in advance. Specifically, each kinetic image is converted through a non-linear warping process or the like so that the lung field region in the reference image substantially coincides with the lung field region in the kinetic image, whereby the respective anatomical structural divisions are recognized.

In the present embodiment, each division of the region divided in step S12 includes a plurality of pixels. Alternatively, each division of the region divided in step S12 may include only a single pixel.

Next, the image analysis unit 47 calculates the analytical values X of the respective divisions in the plurality of time phases based on signal values of the respective divisions in the respective kinetic images (step S13).

The signal value as used herein is a value of each pixel (pixel signal value) of the kinetic image. The intensity of the X-ray that has passed through the object (transmission X-ray intensity) may be used as the signal value. A value expressed in a unit of transmission X-ray intensity, e.g., mR and mGy, may be used as the signal value, or such a value may be converted into a numerical value having a linear relation with the value. For example, transmission X-ray intensities of 0 mR to 1000 mR may be assigned to 12-bit integers (0 to 4095) for use as the signal values. Alternatively, the transmission X-ray intensity or a value having a linear relation with the transmission X-ray intensity may be converted using a predetermined function for use as the signal value. For example, the transmission X-ray intensity may be subjected to a logarithmic transformation for use as the signal value. The description of the present embodiment is based on the premise that the signal value increases in proportion to the strength of the transmission X-ray intensity. Alternatively, the signal value may decrease in proportion to the strength of the transmission X-ray intensity. For example, transmission X-ray intensities of 0 mR to 1000 mR may be assigned to 4095 to 0 for use as the signal values.

The analytical value X as used herein is a value that is calculated on the basis of the signal value in each division. The analytical value X is not particularly limited as long as it represents the X-ray transmission state in the division. For example, a histogram of the signal values of each division is calculated, and the sum obtained by multiplying the signal value corresponding to the lung field by the frequency thereof may be calculated as the analytical value X. Alternatively, a representative value of the signal values in the division, e.g., the average, the median, and the mode or the like, may be calculated as the analytical value X. The average may be a simple average or a weighted average. Alternatively, the calculated representative value may be filtered by a low-pass filter in the time direction for use as the analytical value X. The analytical value X may be the calculated value itself, or a relative value (e.g., difference and ratio) between the analytical value calculated for each frame (kinetic image) and the analytical value calculated for a predetermined frame may be used as the analytical value X.

Alternatively, the analytical value X may be calculated on the basis of the number of pixels in each division. For example, the analytical value X may be the volume obtained by multiplying the area obtained by counting the number of pixels in each division and the thickness of the lung field.

Next, the functions corresponding to the respective divisions, which are stored in the storage unit 44, are acquired by the information acquisition unit 48 for use in the calculation of the index values Y representing the ventilation states (step S14). In the storage unit 44, different functions corresponding to the respective divisions of the region divided in step S12 are stored in association with items of identification information on the respective divisions. As used herein, "different functions corresponding to the respective divisions" indicate that functions for at least two or more divisions of the divided region are different from one another. In a case where, for example, a lot of small divisions are defined, functions for all the divisions do not necessarily need to be different from one another. In other words, two or more different functions corresponding to the respective divisions are stored in the storage unit 44. In the present embodiment, the information acquisition unit 48 reads the functions corresponding to the respective divisions of the region divided in step S12 from the storage unit 44. Alternatively, the functions corresponding to the respective divisions may be stored in the server 50, and the information acquisition unit 48 may acquire the functions from the server 50.

Figure 8:
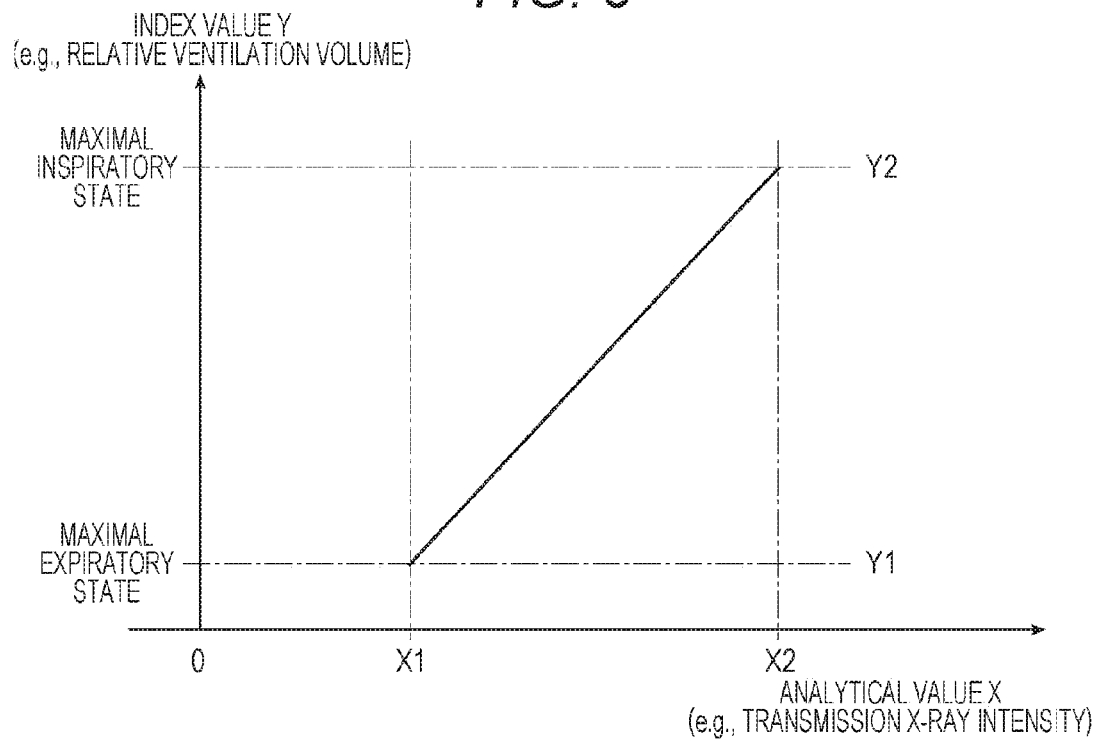
FIG. 8 is a diagram illustrating an exemplary function for use in calculation of the index value from an analytical value.

In FIG. 8, an exemplary function that is acquired in step S14 is illustrated. As illustrated in FIG. 8, the function that is acquired in step S14 is used for the calculation of the index value Y between index values Y1 and Y2 from the analytical value X between analytical values X1 and X2, assuming that the analytical value X is the horizontal axis, the index value Y representing the ventilation state is the vertical axis, the analytical value X in the maximal expiratory phase is X1, the analytical value X in the maximal inspiratory phase is X2, the index value Y indicating the ventilation state in the maximal expiratory phase is Y1, and the index value Y indicating the ventilation state in the maximal inspiratory phase is Y2. The range of X1 to X2 and the range of Y1 to Y2 can be determined on the basis of, without limitation, the relation between the analytical values X and the index values Y typical of a healthy person.

In the present embodiment, the index value Y representing the ventilation state is the relative ventilation volume. However, the index value Y is not particularly limited as long as it is a numerical value representing the ventilation state. As used herein, the ventilation volume in a single respiratory phase is the volume of air that varies during the period between the maximal expiratory phase (phase in which the breath is maximally let out) and the maximal inspiratory phase (phase in which the breath is maximally taken in) illustrated in FIG. 6. To be specific, the ventilation volume in the expiratory phase is the expiratory volume that is let out during the period from the maximal inspiratory phase to the maximal expiratory phase, and the ventilation volume in the inspiratory phase is the inspiratory volume that is taken in during the period from the maximal expiratory phase to the maximal inspiratory phase. The relative ventilation volume as used herein is a numerical value representing the volume of air relative to the entire lung field or a predetermined division of the lung field. For example, the relative ventilation volume may be a real number ranging from 0 to 1 or an integer value ranging from 0 to 4095 (2 bits).

Figure 9:
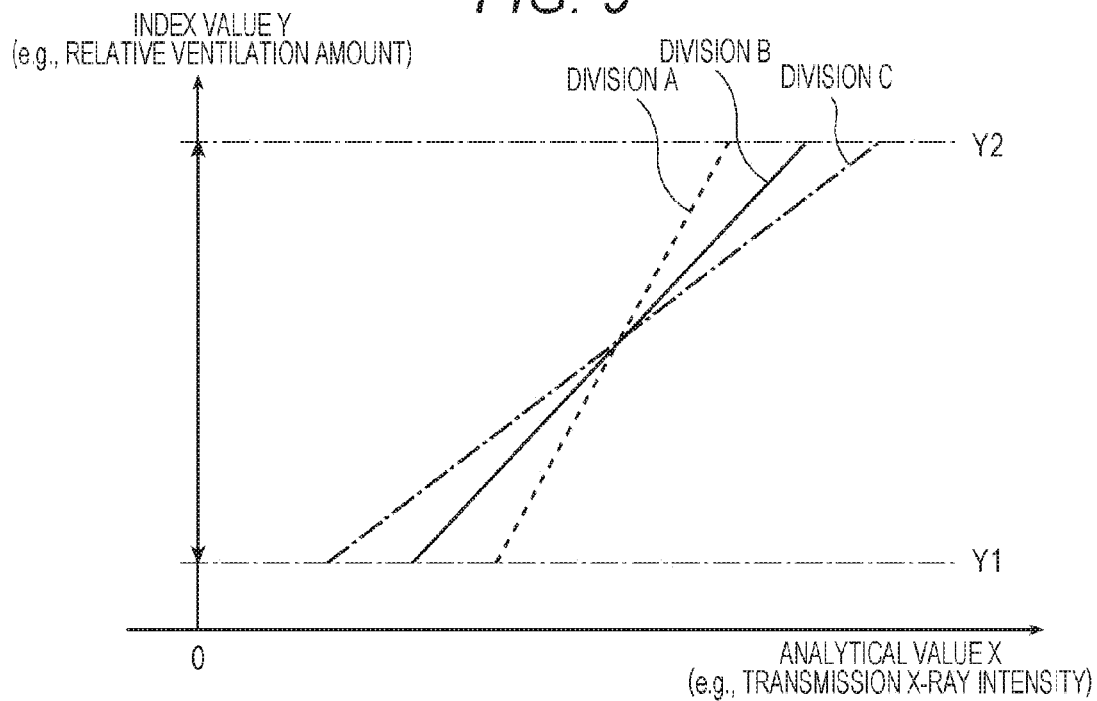
FIG. 9 is a diagram illustrating exemplary functions corresponding to respective divisions A to C illustrated in FIG. 7A.

In FIG. 9, exemplary functions corresponding to the respective divisions A to C of FIG. 7A are illustrated. The ventilation states of all the divisions of the lung field can be determined on the same basis if the index values Y of all the divisions of the lung field vary within the fixed range as illustrated in FIG. 9. In order to ensure that the index values Y of all the divisions of the lung field vary within the fixed range, as illustrated in FIG. 9, the function corresponding to the division A on the upper part of the lung field where the analytical value X slightly varies due to the ventilation preferably has a large absolute value R of the slope, and the function corresponding to the division C on the lower part of the lung field where the analytical value X largely varies due to the ventilation preferably has a small absolute value R of the slope. As used herein, the absolute value R of the slope of the function indicates the ratio ($|Y2-Y1|\div|X2-X1|$) of a difference $|Y2-Y1|$ between the index value Y1 representing the ventilation state in the maximal expiratory phase and the index value Y2 representing the ventilation state in the maximal inspiratory phase to a difference $|X2-X1|$ between the analytical value X1 in the maximal expiratory phase and the analytical value X2 in the maximal inspiratory phase.

Figure 10:
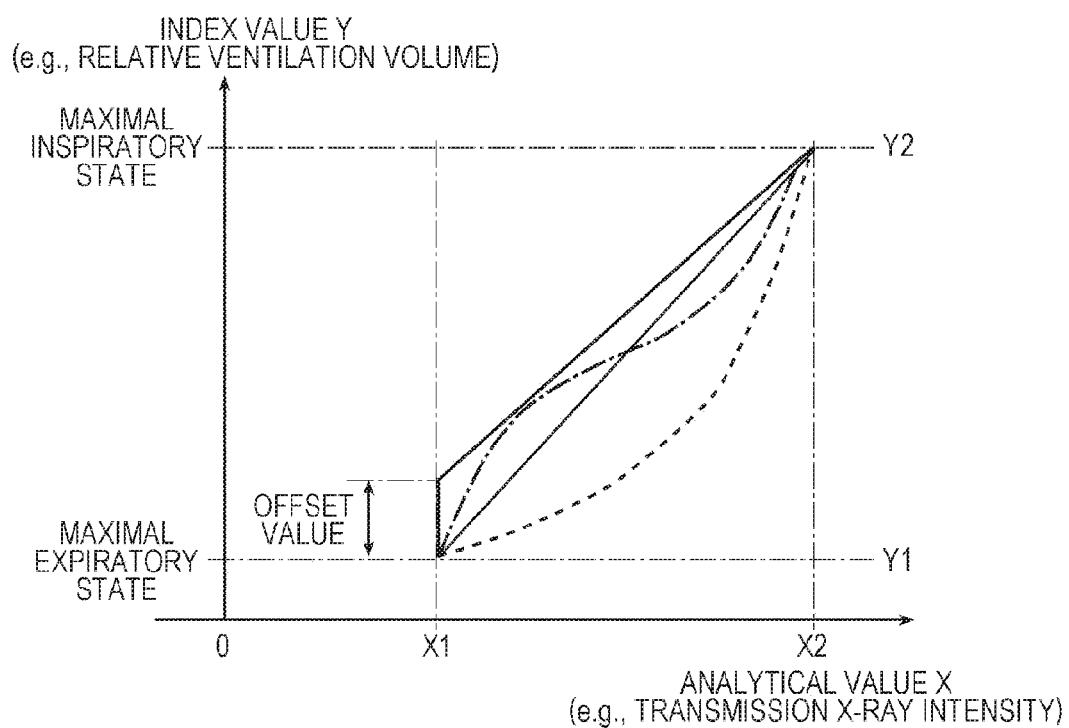
FIG. 10 is a diagram illustrating exemplary shapes of functions.

The functions for the respective divisions may have different shapes such as a linear shape and a non-linear shape as illustrated in FIG. 10. Straight lines having different slopes may be combined. Alternatively, functions having different offset values in the maximal inspiratory phase and/or the maximal expiratory phase (refer to FIG. 10) may be combined. The shape of the function corresponding to each division depends on a combination of the analytical values X and the index values Y.

Figure 11A:
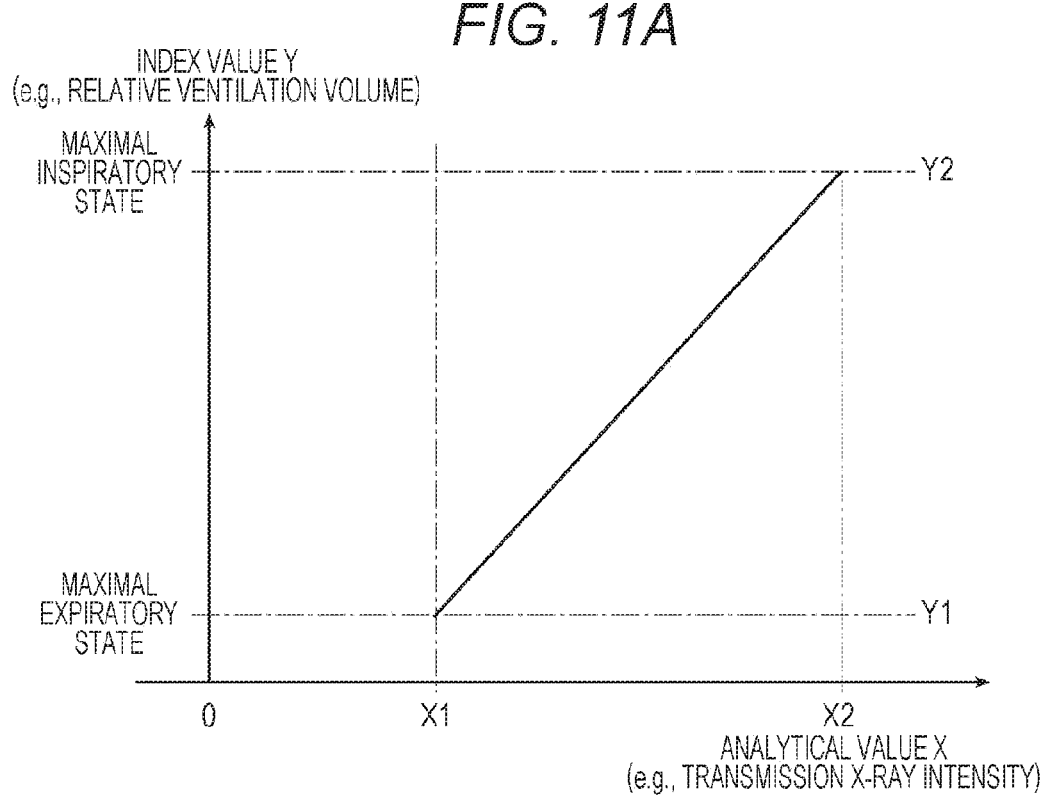
FIG. 11A is a diagram illustrating an exemplary function for an inspiratory phase.
Figure 11B:
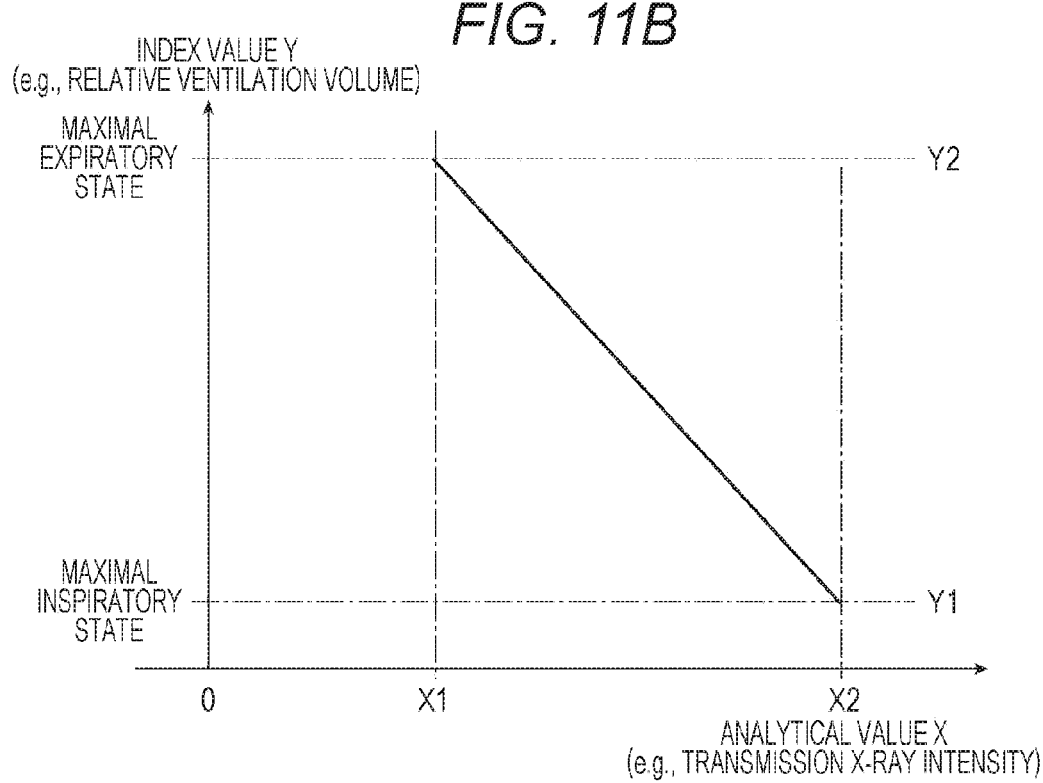
FIG. 11B is a diagram illustrating an exemplary function for an expiratory phase.

Alternatively, different functions may be used for the expiratory phase and the inspiratory phase in each division. For example, as illustrated in FIGS. 11A and 11B, functions may be prepared so that the index value Y for the expiratory phase increases/decreases as the analytical value X increases while the index value Y for the inspiratory phase decreases/increases as the analytical value X increases. As illustrated in FIGS. 11A and 11B, by using such functions that the index value Y for the expiratory phase increases/decreases as the analytical value X increases while the index value Y for the inspiratory phase decreases/increases as the analytical value X increases, the index values Y (i.e., inspiratory volumes) representing the ventilation states in the respective time phases can be calculated in the inspiratory phase based on the premise that the index value Y representing the ventilation state in the maximal expiratory phase is a reference value (e.g., 0), and the index values Y (i.e., expiratory volumes) representing the ventilation states in the respective time phases can be calculated in the expiratory phase based on the premise that the index value Y representing the ventilation state in the maximal inspiratory phase is a reference value (e.g., 0).

Next, the image analysis unit 47 calculates, for the respective divisions in the respective kinetic images, the index values Y representing the ventilation states from the analytical values X using the functions acquired by the information acquisition unit 48 (step S15).

The image analysis unit 47 then attaches, to the kinetic images, items of information on the index values Y representing the ventilation states calculated for the respective divisions in the respective kinetic images in the inspiratory phase and the expiratory phase (step S16). After that, the kinetic images in the respective time phases to which the items of information on the index values Y representing the ventilation states of the respective divisions have been attached are sent to the server 50 via the communication unit 45.

In the server 50, the kinetic images in the respective time phases are collected in a database and saved in the memory together with the attached items of information. In response to a request from the diagnostic console 30, the server 50 sends a group of kinetic images of a patient related to the request.

Returning to FIG. 4, in the diagnostic console 30, the kinetic images in the respective time phases acquired from the server 50 are displayed on the display unit 34 under the display control of the control unit 31 (step S4). At this time, the control unit 31 serially switches the kinetic images in accordance with the time phases, and displays the respective kinetic images as a motion video. This enables the doctor to grasp dynamic changes in the respiratory movement of the lungs.

Generally, the signal value and the analytical value X are displayed on the display device for a plain X-ray image diagnosis in such a manner that the luminance increases (so that the image looks white) in proportion to the weakness of the transmission X-ray intensity, and the luminance decreases (so that the image looks black) in proportion to the strength of the transmission X-ray intensity. Alternatively, black and white may be inverted for display, or the two display styles may be switchably used in accordance with the purpose or preference.

Next, the control unit 31 causes the display unit 34 to display the information on the index values Y representing the ventilation states based on the information attached to the displayed kinetic image (step S5: control unit).

Figure 12A:
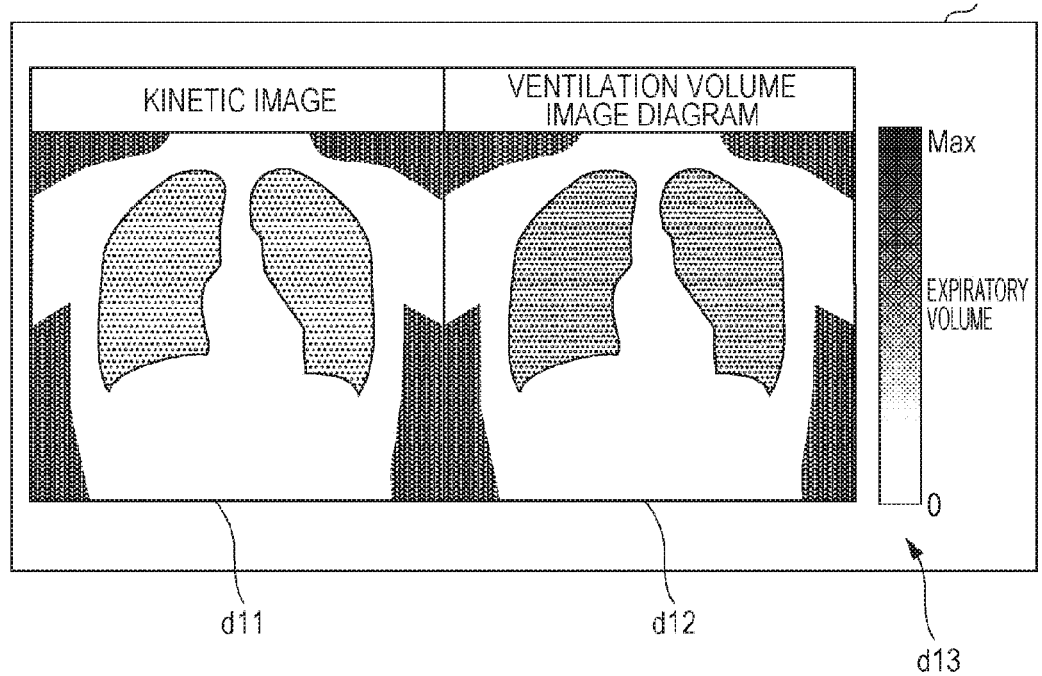
FIG. 12A is a diagram illustrating an exemplary display of the kinetic image and the index values representing the ventilation states.

FIG. 12A is a diagram illustrating an exemplary display of the kinetic image and the index values Y representing the ventilation states.

On a display screen d1 illustrated in FIG. 12A, a display region d11 for the kinetic image and a display region d12 for the index values Y representing the ventilation states are displayed. In the display region d11, the control unit 31 serially switches and displays the kinetic images in accordance with the time phases. In the display region d12 for the index values Y representing the ventilation states, the control unit 31 generates and displays an image diagram indicating the index values Y representing the ventilation states calculated for each kinetic image. In the image diagram indicating the index values Y representing the ventilation states, the index values Y representing the ventilation states of the respective divisions in each kinetic image are represented by colors corresponding to the index values Y. An indicator d13 indicating the correspondence between the color density and the ventilation volume is displayed adjacent to the display region d12. In the indicator d13, the lower limit of the relative ventilation volume, namely, the index value Y, is denoted by 0, and the upper limit is denoted by Max. Furthermore, the control unit 31 may display, using numerical values, the index values Y representing the ventilation states of the respective divisions calculated for each kinetic image.

Figure 12B:
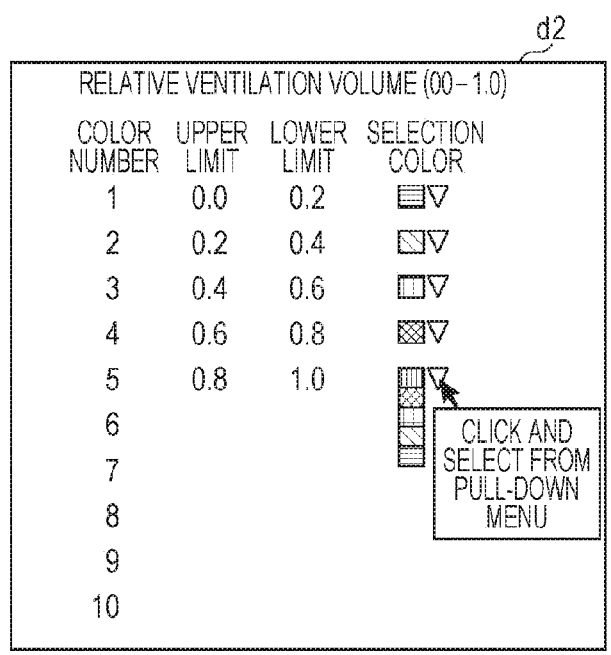
FIG. 12B is a diagram illustrating an exemplary user interface screen for correlating the index values representing the ventilation states with display colors.

In the image diagram, the colors corresponding to the index values Y representing the ventilation states may be represented by different tones of a single color hue such as white, red, blue, and green, or may be represented by a plurality of different color hues. For example, 0 to 0.2, 0.2 to 0.4, 0.4 to 0.6, 0.6 to 0.8, and 0.8 to 1.0 of the relative ventilation volumes (0 to 1) can be displayed in blue, green, yellow, orange, and red, respectively. The correlations between the index values Y representing the ventilation states and the display colors (tones or hues) are preferably selected on a user interface screen d2 displayed as illustrated in FIG. 12B in accordance with the user's preference.

Figure 13:
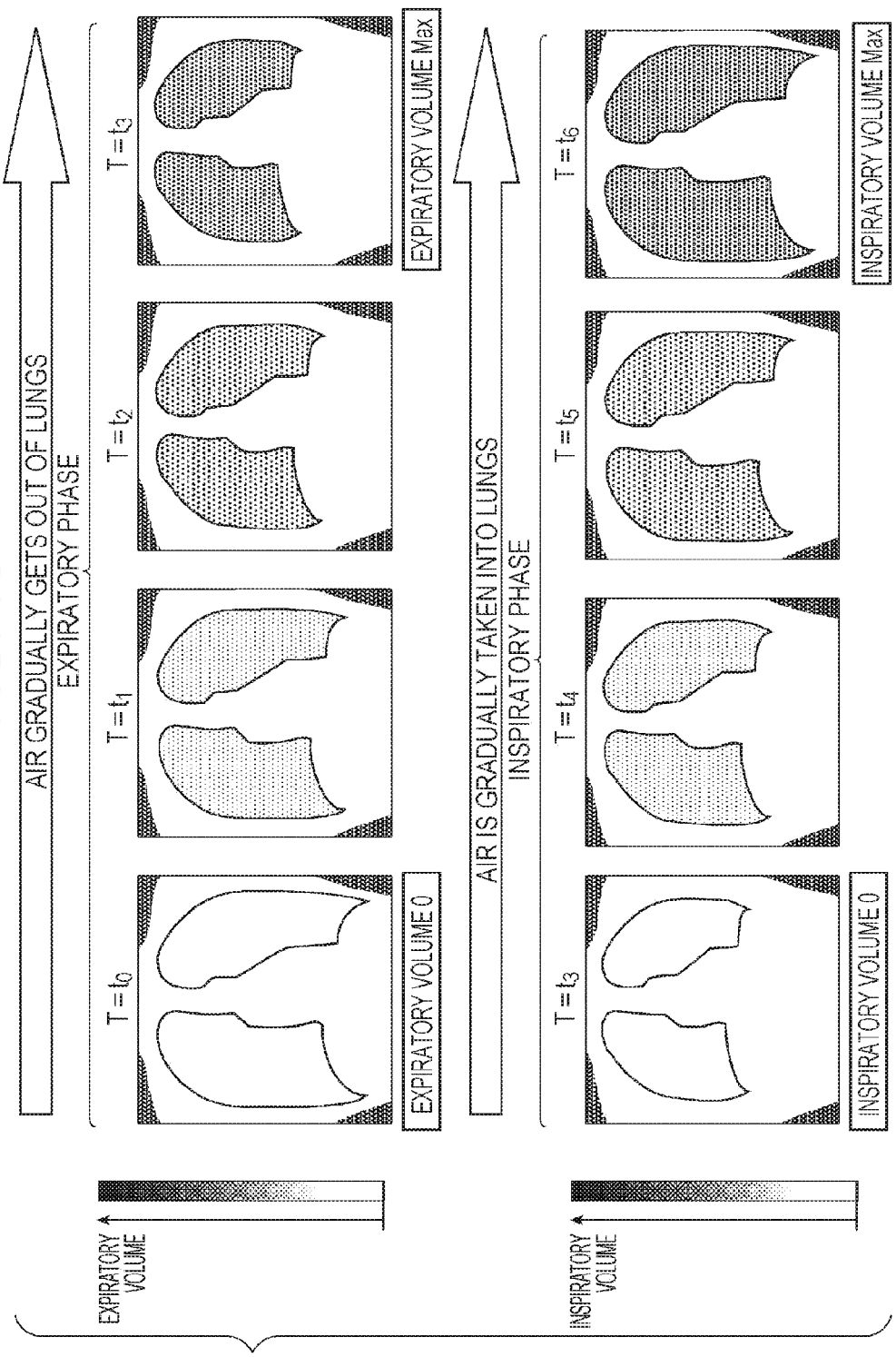
FIG. 13 is image diagrams of the index values representing the ventilation states of a healthy person.
Figure 14:
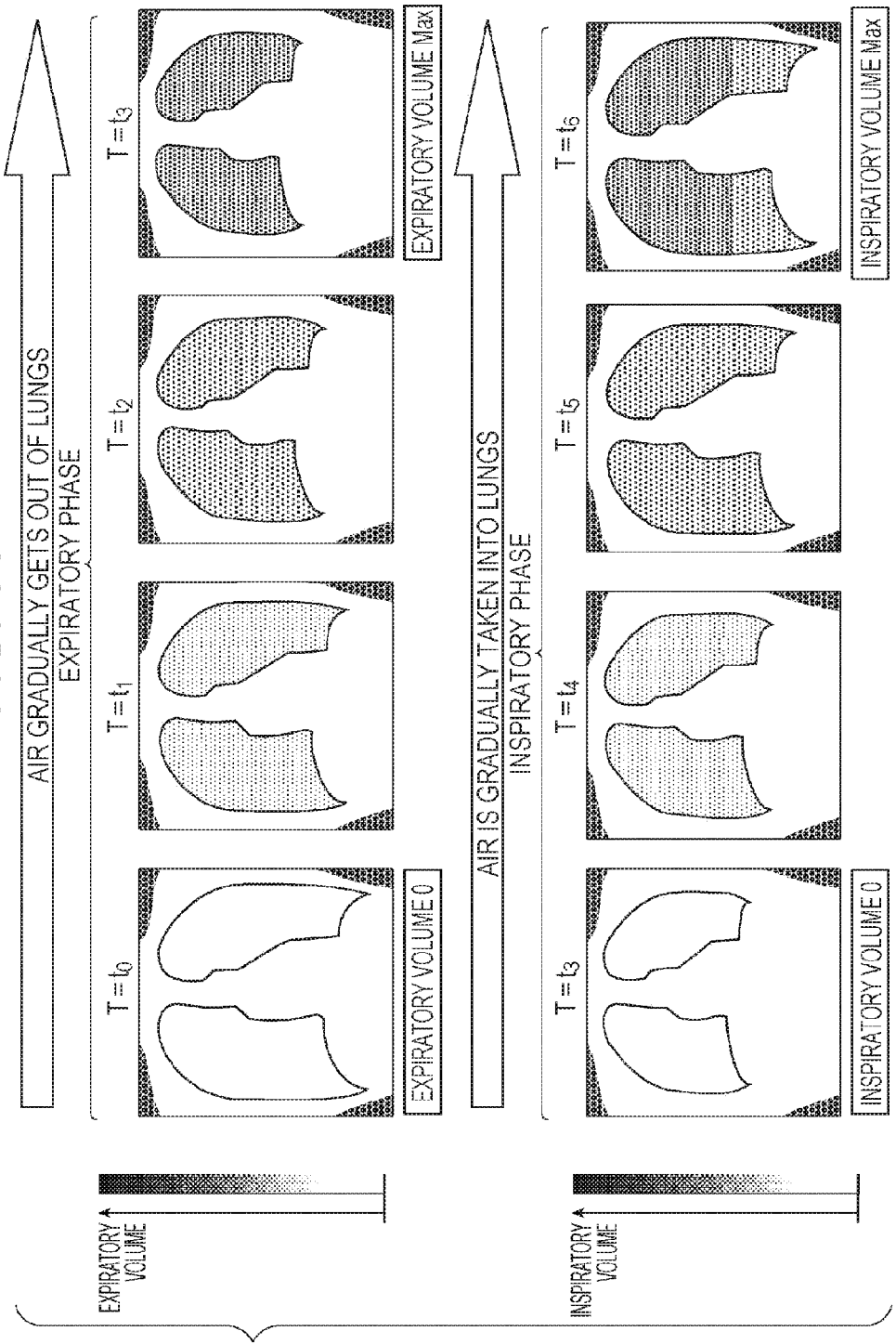
FIG. 14 is image diagrams of the index values representing the ventilation states of a patient with a disease in the lower part of the lung field.

In FIGS. 13 and 14, exemplary image diagrams indicating the index values Y representing the ventilation states are illustrated. FIGS. 13 and 14 illustrate the index values Y calculated using such functions that the index value Y for the expiratory phase increases/decreases as the analytical value X increases while the index value Y for the inspiratory phase decreases/increases as the analytical value X increases as illustrated in FIGS. 11A and 11B. FIG. 13 is the image diagrams indicating the index values Y representing the ventilation states of a healthy person, and FIG. 14 is the image diagrams indicating the index values Y representing the ventilation states of a patient with a disease in the lower part of the lung field. The upper part of each of FIGS. 13 and 14 indicates the relative ventilation volumes (expiratory volumes) in the expiratory phase, and the lower part of each of FIGS. 13 and 14 indicates the relative ventilation volumes (inspiratory volumes) in the inspiratory phase.

As illustrated in FIGS. 13 and 14, in the expiratory phase, the respective divisions in the kinetic images in the respective time phases $T=t_0, t_1, t_2,$ and $t_3$ are represented by the colors corresponding to the expiratory volumes of the respective divisions, assuming that the expiratory volume in the kinetic image in the maximal inspiratory phase (time phase $T=t_0$) is 0. Consequently, variations in the expiratory volume can be visually indicated with reference to the expiratory volume in the maximal inspiratory phase. The expiratory volume in the kinetic image in the maximal inspiratory phase can be set to 0 simply by subtracting Y1 from the index value Y.

The same applies to the inspiratory phase. As illustrated in FIGS. 13 and 14, in the inspiratory phase, the respective divisions in the kinetic images in the respective time phases $T=t_3, t_4, t_5,$ and $t_6$ are represented by the colors corresponding to the inspiratory volumes of the respective divisions, assuming that the inspiratory volume in the kinetic image in the maximal expiratory phase (time phase $T=t_3$) is 0. Consequently, variations in the inspiratory volume can be visually indicated with reference to the inspiratory volume in the maximal expiratory phase. The inspiratory volume in the kinetic image in the maximal expiratory phase can be set to 0 simply by subtracting Y1 from the index value Y.

Figure 18A:
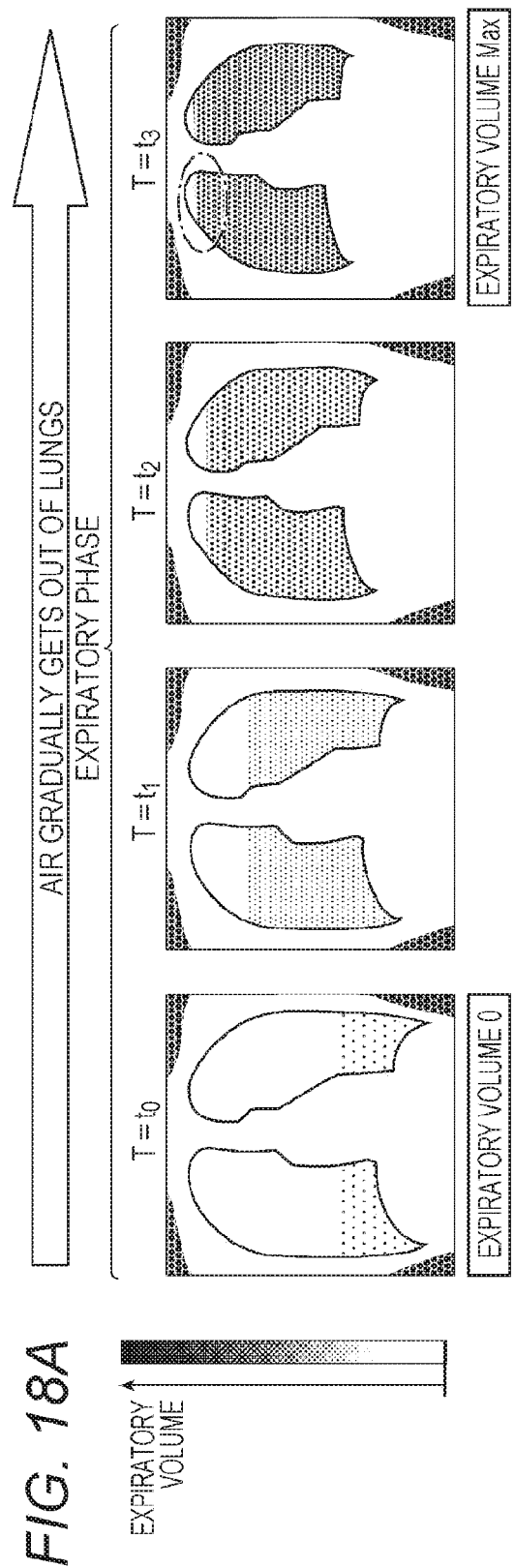
FIG. 18A is image diagrams of the estimated ventilation volumes of the healthy person according to the related art.

In a case where the index values Y representing the ventilation states are calculated as in the related art using the same function for the entire lung field, since different divisions of the lung field have different absolute ventilation volumes, the image diagrams for a healthy person are displayed as if the ventilation states varied in different divisions even though the ventilation states of all the divisions are normal. This might cause such a misunderstanding that, for example, the ventilation of the upper part of the lung field where the absolute ventilation volume is naturally small does not sufficiently function (refer to FIG. 18A). In the present embodiment, the index values Y representing the ventilation states are calculated using the functions corresponding to the respective divisions. Therefore, the ventilation state can be evaluated in consideration of the difference between the absolute ventilation volumes of the respective divisions, and the respective divisions can be indicated using the same display mode in a case where the ventilation states of all the divisions are normal as illustrated in FIG. 13.

Figure 18B:
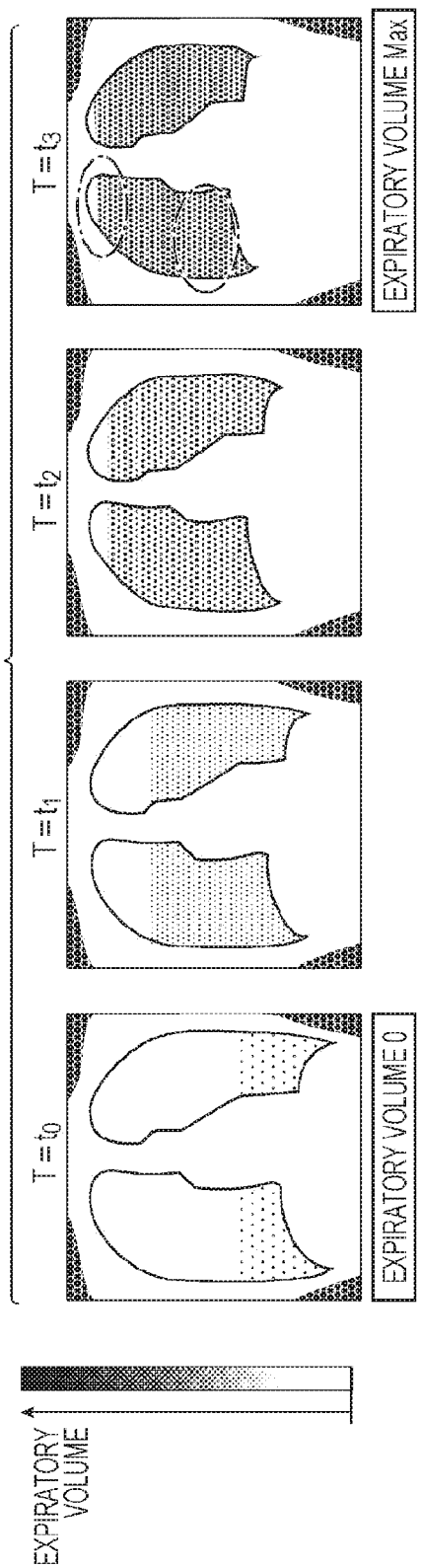
FIG. 18B is image diagrams of the estimated ventilation volumes of the patient with the disease in the lower part of the lung field according to the related art.

In a case where the index values Y representing the ventilation states are calculated as in the related art using the same function for the entire lung field, display of the image diagrams for a patient with a disease in the lower part of the lung field might cause such a misunderstanding that the ventilation of the lower part of the lung field sufficiently functions due to overvaluation of the ventilation of the lower part of the lung field where the original absolute ventilation volume is large (refer to FIG. 18B). In the present embodiment, the index values Y representing the ventilation states are calculated using the functions corresponding to the respective divisions. Therefore, the ventilation state can be evaluated in consideration of the difference between the absolute ventilation volumes of the respective divisions, and dysfunction of the ventilation of the lower part of the lung field can be indicated as illustrated in FIG. 14.

The control unit 31 serially switches and displays the image diagrams in the display region d12 in accordance with the time phases, with the respective divisions in the respective kinetic images represented by the colors corresponding to the index values Y representing the ventilation states. The color variations for the image diagrams enable the doctor to visually grasp the variations in the index values Y representing the ventilation states as time passes.

The image diagrams are switched and displayed in synchronization with the time phases for the original kinetic images in the display region d11. Since the image diagrams are displayed in conjunction with the original kinetic images, the information on the index values Y representing the ventilation states can be referred to while the original kinetic image is observed.

Figure 15:
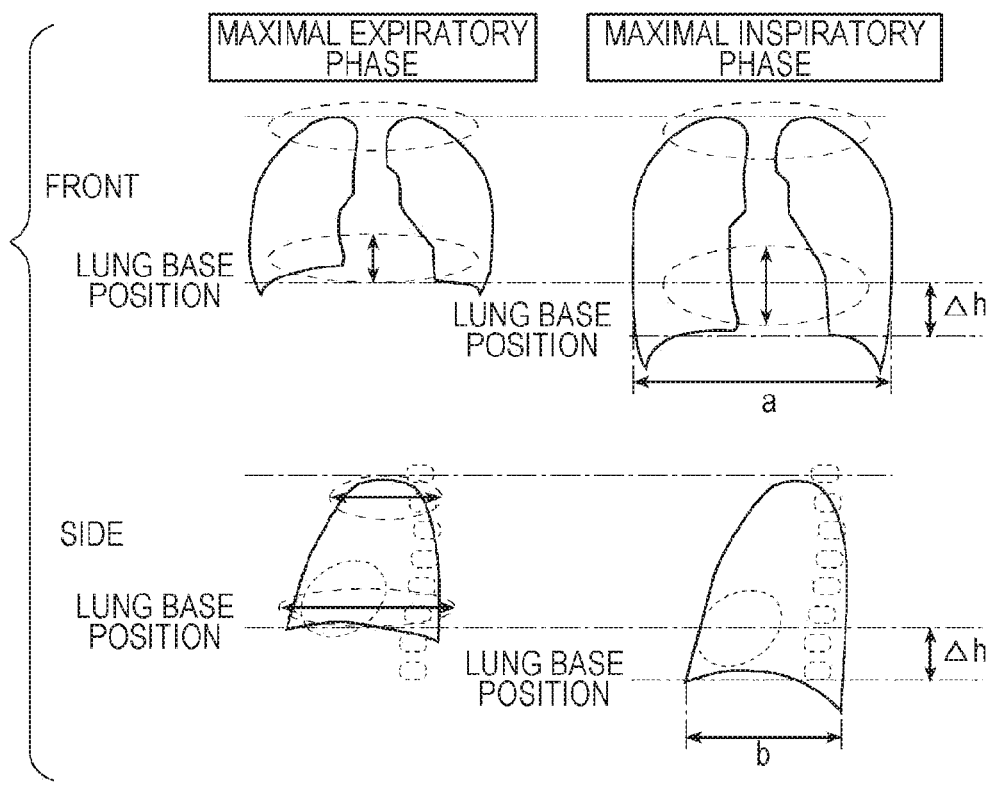
FIG. 15 is a diagram illustrating kinetic images photographed from the front and the side in a maximal expiratory phase and a maximal inspiratory phase.
Figure 16A:
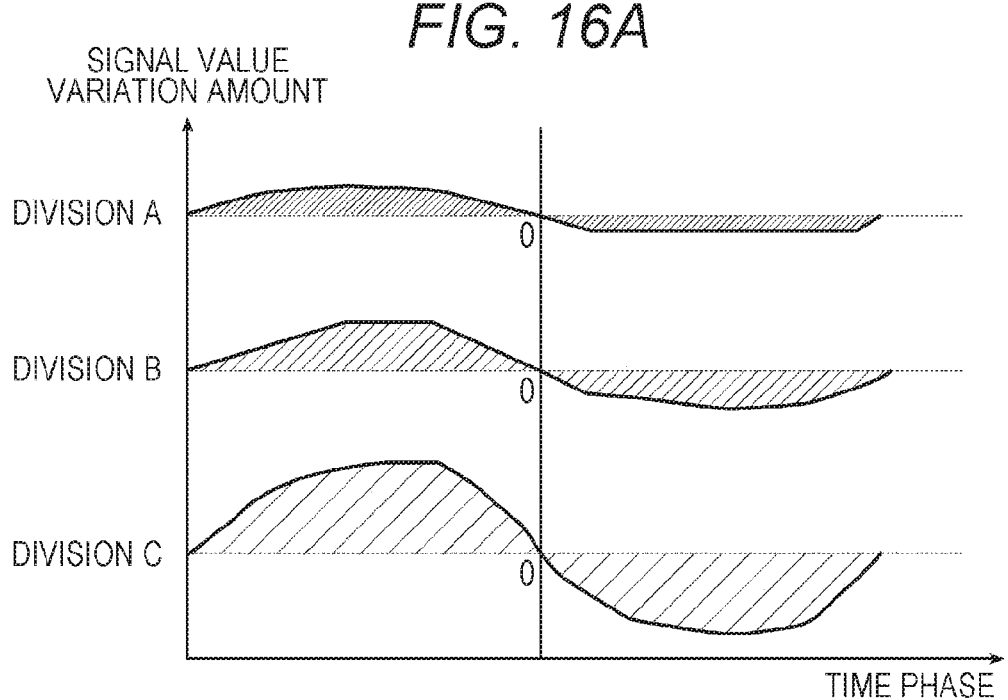
FIG. 16A is a diagram illustrating the signal value variation amounts of the respective divisions of a healthy person.
Figure 16B:
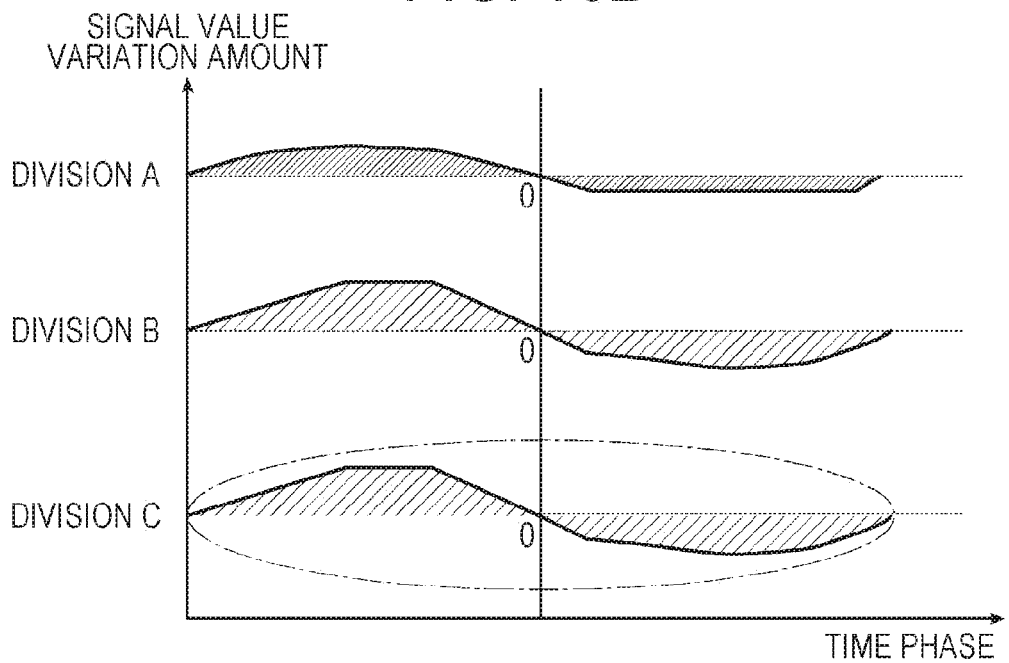
FIG. 16B is a diagram illustrating the signal value variation amounts of the respective divisions of a patient with a disease in the division C.
Figure 17A:
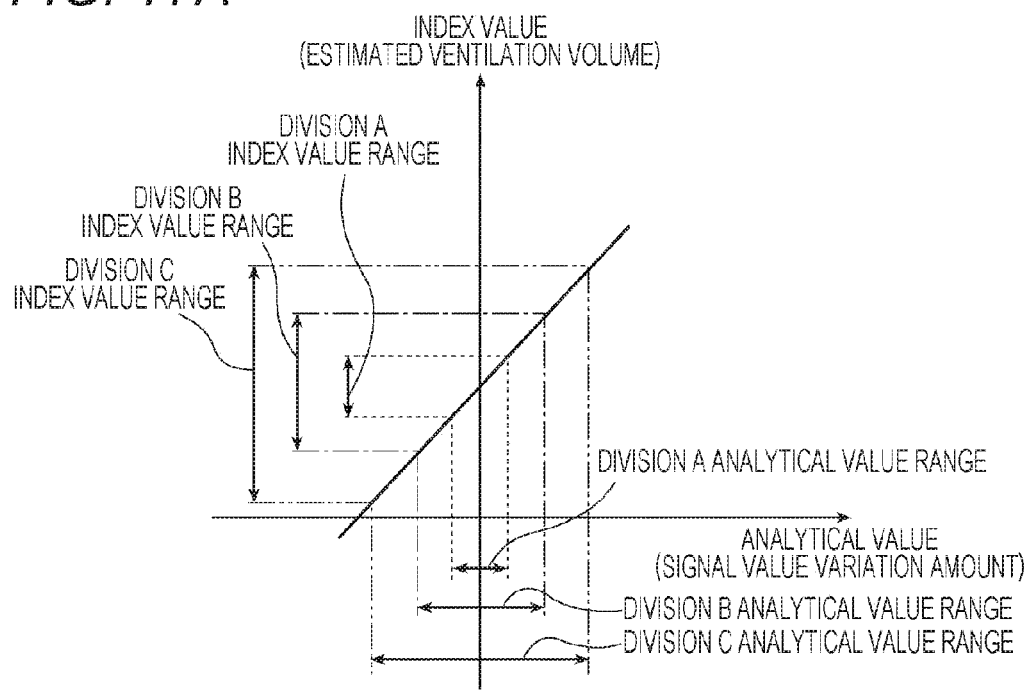
FIG. 17A is a diagram illustrating a function for calculating the estimated ventilation volumes from the signal value variation amounts, ranges of the signal value variation amounts of the respective divisions of the healthy person, and ranges of the estimated ventilation volumes of the respective divisions of the healthy person according to the related art.
Figure 17B:
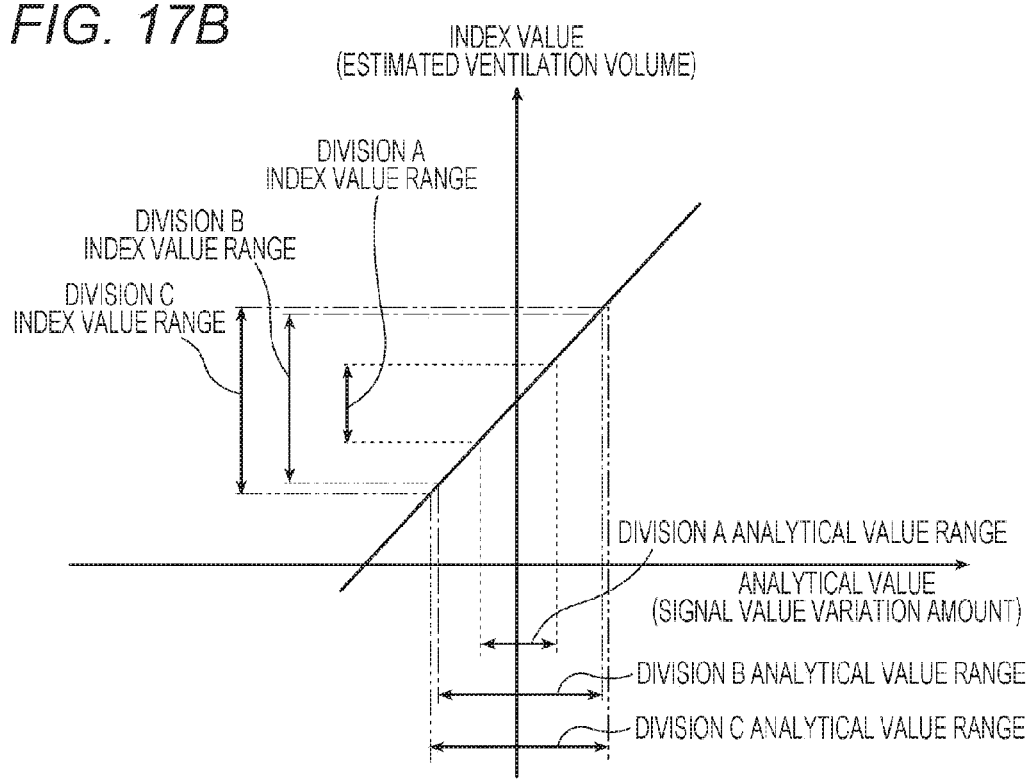
FIG. 17B is a diagram illustrating a function for calculating the estimated ventilation volumes from the signal value variation amounts, ranges of the signal value variation amounts of the respective divisions of the patient with the disease in the division C, and ranges of the estimated ventilation volumes of the respective divisions of the patient according to the related art.

In a case where the relative ventilation volume is obtained as the index value Y, a value of the absolute ventilation volume corresponding to the analytical value X can also be obtained on the basis of the relative ventilation volume. The absolute ventilation volume is a measured value of the ventilation amount or a value substantially equal to the measured value. For example, the absolute ventilation volume is the ventilation volume measured with a spirometer (tidal volume, forced vital capacity or the like). Alternatively, the absolute ventilation volume can be the volume V obtained in the following manner. Specifically, lung bases are detected from the kinetic images in the maximal expiratory phase and the maximal inspiratory phase. Then, Δh is obtained from a difference between the positions of the lung bases, the length a and the thickness b of the lung base are obtained (refer to FIG. 15), and the volume V is calculated using Δh, the length a, and the thickness b. The absolute ventilation volume corresponding to the analytical value X can be obtained by multiplying the vertical axis by a predetermined coefficient so that among the relative ventilation volumes (index values Y) obtained from the analytical values X, a difference between the index values Y for the maximal inspiratory phase and the maximal expiratory phase corresponds to the absolute ventilation volume acquired in a different manner (for example, measured with a spirometer). In a case where the absolute ventilation volume is obtained in each of the plurality of divisions, the sum of the differences between the index values Y for the maximal inspiratory phase and the maximal expiratory phase in the respective divisions only needs to be equal to the absolute ventilation volume acquired in the above-mentioned different manner.

As mentioned above, according to the present embodiment, the image analysis unit 47 of the image processing device 40 divides, into the plurality of divisions, the lung field region included in the kinetic images in the plurality of time phases generated as the result of the kymography of the chest of the object, calculates the analytical values X of the respective divisions in the plurality of time phases based on at least one of the pixel signal values and the number of pixels in the respective divisions, and calculates the index values Y representing the ventilation states of the respective divisions from the analytical values X of the respective divisions using the different functions corresponding to the respective divisions. The control unit 41 causes the display unit 43 to display the index values Y representing the ventilation states of the respective divisions in the plurality of time phases. Therefore, since the index values Y representing the ventilation states are calculated using the functions corresponding to the respective divisions of the lung field, the ventilation state of each division can be displayed more accurately, and the doctor or the like can grasp the ventilation state of each division of the lung field more accurately.

For example, the image analysis unit 47 uses a function having a large absolute value of the slope for the upper division of the lung field region and uses a function having a small absolute value of the slope for the lower division of the lung field region. As a result, the index values Y of the respective divisions can be calculated within the fixed range, and the ventilation states of all the divisions of the lung field can be represented on the same basis. Therefore, the doctor or the like can grasp the ventilation state of each division of the lung field more accurately.

The above-mentioned embodiment is only a preferable example of the present invention, and the present invention is not limited to this embodiment.

For example, according to the above-mentioned embodiment, only a single combination of functions corresponding to the respective divisions is stored in the storage unit 44. Alternatively, a plurality of patterns of combinations of functions corresponding to the respective divisions may be stored in the storage unit 44, a pattern to be actually used for the calculation of the index values Y may be selected by a selection unit (not illustrated) from among the plurality of patterns stored in the storage unit 44, and the functions included in the selected pattern may be acquired by the information acquisition unit 48. The selection unit may automatically select a pattern that is used for the calculation of the index values Y based on, for example, the information attached to the kinetic image, or select a pattern in accordance with the operation for the operation unit 42.

For example, in a case where the object is photographed in the standing posture, an extension/contraction state of an alveolus in the upper lung field is significantly different from that in the lower lung field due to the influence of gravity, as compared with a case where the object is photographed in the lying posture. In this regard, for example, a pattern of functions for the upper lung field and the lower lung field having a large difference between the absolute values R of the slopes and a pattern of functions for the upper lung field and the lower lung field having a small difference between the absolute values R of the slopes may be stored in the storage unit 44. In a case where the examination information attached to the kinetic image indicates that the object has been photographed in the standing posture, the selection unit may select the pattern of functions for the upper lung field and the lower lung field having a large difference between the absolute values R of the slopes. In a case where the examination information attached to the kinetic image indicates that the object has been photographed in the lying posture, the selection unit may select the pattern of functions for the upper lung field and the lower lung field having a small difference between the absolute values R of the slopes. Consequently, the index values Y indicating the ventilation states can be calculated in further consideration of the influence of gravity at the time of photography.

In addition, for example, a pattern of a combination of different functions for the respective divisions and a pattern of a combination of the same function for the respective divisions may be stored in the storage unit 44, and either pattern may be selected through the operation for the operation unit 42 as a pattern that is actually used for the calculation of the index values Y. Consequently, for example, the index values Y representing the ventilation states can be displayed in a manner convenient for the user (doctor).

According to the above-mentioned embodiment, the functions corresponding to the respective divisions are stored in the storage unit 44 in advance. Alternatively, the image processing device 40 may be configured to include a setting unit that sets the functions corresponding to the respective divisions in accordance with user operation. For example, a plurality of functions having different slopes and shapes may be stored in the storage unit 44 in advance, and the control unit 41 may display, on the display unit 43, a user interface for setting the functions corresponding to the respective divisions from among the plurality of functions stored in the storage unit 44 in accordance with an instruction to the operation unit 42 from the user Then, the image analysis unit 47 may calculate the index values Y representing the ventilation states using the functions set for the respective divisions by the operation unit 42 on the user interface.

The functions of the selection unit and the setting unit mentioned above can be realized by the control unit 41 that operates in cooperation with programs.

In the above-described configuration, the index values Y representing the ventilation states are displayed on the diagnostic console 30. Alternatively, the index values Y may be displayed on the photographing console 20 or another device (such as a PC for use in diagnosis). In the above-described configuration, the image processing device 40 that analyzes the images is provided, and the index values Y representing the ventilation states are calculated in the image processing device 40. Alternatively, a program for calculating the above-mentioned index values Y representing the ventilation states may be installed on the diagnostic console 30 or another device for the calculation of the index values Y.

A portable medium such as a DVD as well as a memory such as a ROM can be employed as a computer-readable medium that stores the programs according to the above-described processes. A carrier wave can be employed as a medium for providing data of the programs via the network.

The detailed configuration and the detailed operation of each device constituting the kinetic analysis system can be appropriately changed in a range not departing from the gist of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:
1. A kinetic analysis system comprising:
an analytical value calculation unit configured to divide, into a plurality of divisions, a lung field region included in kinetic images in a plurality of time phases acquired as a result of kymography of a chest of an object, and calculate analytical values of the respective divisions in the plurality of time phases based on at least one of pixel signal values and the number of pixels in the respective divisions;

a ventilation state calculation unit configured to calculate index values representing ventilation states of the respective divisions from the analytical values of the respective divisions in the plurality of time phases using different functions corresponding to the respective divisions;

a display unit; and a control unit configured to cause the display unit to display the index values representing the ventilation states of the respective divisions in the plurality of time phases.

2. The kinetic analysis system according to claim 1, wherein the ventilation state calculation unit calculates the index values representing the ventilation states of the respective divisions from the analytical values of the respective divisions in the plurality of time phases using a function having a large absolute value of a slope for an upper division of the lung field region and using a function having a small absolute value of a slope for a lower division of the lung field region.

3. The kinetic analysis system according to claim 1, wherein the ventilation state calculation unit calculates the index values representing the ventilation states of the respective divisions from the analytical values of the respective divisions in the plurality of time phases using such functions that offset values for the respective divisions in a maximal inspiratory phase and/or a maximal expiratory phase are different from each other.

4. The kinetic analysis system according to claim 1, further comprising:

a storage unit configured to store the functions corresponding to the respective divisions; and an information acquisition unit configured to acquire the functions corresponding to the respective divisions from the storage unit, wherein the ventilation state calculation unit calculates the index values representing the ventilation states of the respective divisions using the functions corresponding to the respective divisions acquired by the information acquisition unit.

5. The kinetic analysis system according to claim 4, wherein the storage unit stores a plurality of patterns of combinations of functions corresponding to the respective divisions, the kinetic analysis system further includes a selection unit configured to select, from among the plurality of patterns stored in the storage unit, a pattern that is used by the ventilation state calculation unit for calculation of the index values, and the ventilation state calculation unit calculates the index values of the respective divisions using functions included in the pattern selected by the selection unit.

6. The kinetic analysis system according to claim 5, wherein the selection unit selects a pattern that is used by the ventilation state calculation unit for calculation of the index values based on information as to whether the object has been photographed in a standing posture or a lying posture.

7. The kinetic analysis system according to claim 6, wherein in a case where the object has been photographed in the standing posture, the selection unit selects such a pattern that a difference between an absolute value of a slope of a function for an upper division of the lung field region and an absolute value of a slope of a function for a lower division of the lung field region is large, as compared with a case where the object has been photographed in the lying posture.

8. The kinetic analysis system according to claim 1, further comprising a setting unit configured to set the functions corresponding to the respective divisions in accordance with user operation.

9. The kinetic analysis system according to claim 1, wherein the ventilation state calculation unit calculates the index values from the analytical values using different functions for an expiratory phase and an inspiratory phase.

10. The kinetic analysis system according to claim 9, wherein the ventilation state calculation unit uses such functions that the index value for the expiratory phase increases/decreases as the analytical value increases while the index value for the inspiratory phase decreases/increases as the analytical value increases.

11. The kinetic analysis system according to claim 1, wherein the control unit generates image diagrams indicating the index values of the respective divisions calculated for the respective kinetic images in the plurality of time phases, and serially switches and displays the image diagrams on the display unit in accordance with the time phases.

12. The kinetic analysis system according to claim 1, wherein the functions are linear functions.

13. The kinetic analysis system according to claim 1, wherein the functions are non-linear functions.

14. The kinetic analysis system according to claim 1, wherein the analytical value calculation unit calculates the analytical values based on transmission X-ray intensities in the respective divisions.

15. The kinetic analysis system according to claim 1, wherein the ventilation state calculation unit calculates relative ventilation volumes as the index values.

16. The kinetic analysis system according to claim 1, further comprising a photographing unit configured to perform the kymography on the chest of the object to generate the kinetic images in the plurality of time phases.

* * * * *